US012417843B2

(12) United States Patent
Neumann

(10) Patent No.: US 12,417,843 B2
(45) Date of Patent: Sep. 16, 2025

(54) METHODS AND SYSTEMS FOR CONFIRMING AN ADVISORY INTERACTION WITH AN ARTIFICIAL INTELLIGENCE PLATFORM

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

(*) Notice: Subject to any disclaimer, the term of this patent is extended or adjusted under 35 U.S.C. 154(b) by 1193 days.

(21) Appl. No.: 17/164,491

(22) Filed: Feb. 1, 2021

(65) Prior Publication Data

US 2021/0183515 A1    Jun. 17, 2021

Related U.S. Application Data

(63) Continuation-in-part of application No. 17/032,050, filed on Sep. 25, 2020, now Pat. No. 12,087,442, (Continued)

(51) Int. Cl.
*G16H 50/20* (2018.01)
*G06N 20/00* (2019.01)
*G16H 70/20* (2018.01)

(52) U.S. Cl.
CPC ........... *G16H 50/20* (2018.01); *G06N 20/00* (2019.01); *G16H 70/20* (2018.01)

(58) Field of Classification Search
CPC ........ G16H 50/20; G16H 70/20; G06N 20/00
See application file for complete search history.

(56) References Cited

U.S. PATENT DOCUMENTS 9,460,400 B2    10/2016    De Bruin et al.
10,332,624 B2    6/2019    Berdia
(Continued)

FOREIGN PATENT DOCUMENTS

WO    2019155267    8/2019

OTHER PUBLICATIONS

Yin, Hongxu, and Niraj K. Jha. "A health decision support system for disease diagnosis based on wearable medical sensors and machine learning ensembles." IEEE Transactions on Multi-Scale Computing Systems 3.4 (2017): 228-241. (Year: 2017).*
(Continued)

*Primary Examiner* — Kevin W Figueroa
(74) *Attorney, Agent, or Firm* — Caldwell Intellectual Property Law

(57) ABSTRACT

A system for confirming an advisory interaction with an artificial intelligence platform. The system includes a constitutional generator module configured to receive a first advisory input, retrieve an expert input, select a machine-learning process as a function of the expert input, and generate a therapeutic corrector. The system includes a constitutional advisory module configured to display a therapeutic corrector on a graphical user interface and receive a second advisory input. The system includes a best practices module the best practices module designed and configured to retrieve from an expert database a best practices training set, calculate an optimal vector output, generate an optimal vector output containing an expected therapeutic corrector implementation response, authenticate a second advisory input, and update the best practices module.

20 Claims, 11 Drawing Sheets

Related U.S. Application Data which is a continuation-in-part of application No. 16/671,925, filed on Nov. 1, 2019, now Pat. No. 10,936,962.

(56) References Cited

U.S. PATENT DOCUMENTS

| | | | |
|---|---|---|---|
| 2014/0279746 A1* | 9/2014 | De Bruin | G16H 50/70 |
| | | | 706/46 |
| 2015/0120319 A1 | 4/2015 | Wilson | |
| 2017/0124269 A1 | 5/2017 | McNair et al. | |
| 2017/0277841 A1* | 9/2017 | Shankar | G16Z 99/00 |
| 2018/0137941 A1 | 5/2018 | Chen | |
| 2018/0342323 A1 | 11/2018 | Shankar et al. | |
| 2019/0043610 A1 | 2/2019 | Vaughan | |
| 2019/0295719 A1 | 9/2019 | Logan et al. | |

OTHER PUBLICATIONS

Jiang, Fei, et al. "Artificial intelligence in healthcare: past, present and future." Stroke and vascular neurology 2.4 (2017): 230-243. Retrieved on Oct. 14, 2019 from https://svn.bmj.com/content/svnbmj/2/4/230.full.pdf.

Diprose, William, and Nicholas Buist. "Artificial intelligence in medicine: humans need not apply?." The New Zealand Medical Journal (Online) 129.1434 (2016): 73. Retrieved on Oct. 14, 2019 from https://www.researchgate.net/profile/William-Diprose/publication/303019481_Artificial_intelligence_in_medicine_Humans_need_not_apply/links/5735b78c08aea45ee83c98e3/Artificial-intelligence-in-medicine-Humans-need-not-apply.pdf.

* cited by examiner

METHODS AND SYSTEMS FOR CONFIRMING AN ADVISORY INTERACTION WITH AN ARTIFICIAL INTELLIGENCE PLATFORM

CROSS-REFERENCE TO RELATED APPLICATIONS

This application is a continuation-in-part of U.S. Nonprovisional application Ser. No. 17/032,050, filed on Sep. 25, 2020 and entitled "METHODS AND SYSTEMS FOR CONFIRMING AN ADVISORY INTERACTION WITH AN ARTIFICIAL INTELLIGENCE PLATFORM," which is a continuation-in-part of U.S. Non-provisional application Ser. No. 16/671,925 filed on Nov. 1, 2019 and entitled "METHODS AND SYSTEMS FOR CONFIRMING AN ADVISORY INTERACTION WITH AN ARTIFICIAL INTELLIGENCE PLATFORM." Each of U.S. Nonprovisional application Ser. No. 17/032,050 and U.S. Non-provisional application Ser. No. 16/671,925 is incorporated herein by reference in its entirety.

FIELD OF THE INVENTION

The present invention generally relates to the field of artificial intelligence. In particular, the present invention is directed to methods and systems for confirming an advisory interaction with an artificial intelligence platform.

BACKGROUND

Accurate selection and authentication of data entries to be incorporated into an artificial intelligence platform can be challenging. Selection of inaccurate data entries can create data entries that do not produce accurate or informative results.

SUMMARY OF THE DISCLOSURE

In an aspect, a system for confirming an advisory interaction with an artificial intelligence platform includes a processor connected to a memory, wherein the processor is further configured to receive a first advisory input containing a constitutional inquiry and a user identifier from an advisor client device operated by an informed advisor, retrieve an expert input from an expert database operating on the processor as a function of the first advisory input and the user identifier, select a machine-learning process as a function of the expert input, generate a therapeutic corrector utilizing the machine-learning process and the first advisory input wherein the therapeutic corrector further comprises a response to the constitutional inquiry, display the therapeutic corrector on a graphical user interface located on the processor, obtain an adherence input from the advisor client device, calculate an inference model as a function of the adherence input, and update the expert database as a function of the inference model and therapeutic corrector.

In another aspect, a method for confirming an advisory interaction with an artificial intelligence platform includes receiving, by a processor, a first advisory input containing a constitutional inquiry and a user identifier from an advisor client device operated by an informed advisor, retrieving, by the processor, an expert input from an expert database operating on the processor as a function of the first advisory input and the user identifier, selecting, by the processor, a machine-learning process as a function of the expert input, generating, by the processor, a therapeutic corrector utilizing the machine-learning process and the first advisory input wherein the therapeutic corrector further comprises a response to the constitutional inquiry, displaying, by the processor, the therapeutic corrector on a graphical user interface located on the processor, obtaining, by the processor, an adherence input from the advisor client device, calculating, by the processor, an inference model as a function of the adherence input, and updating, by the processor, the expert database as a function of the inference model and therapeutic corrector.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Figure 1:
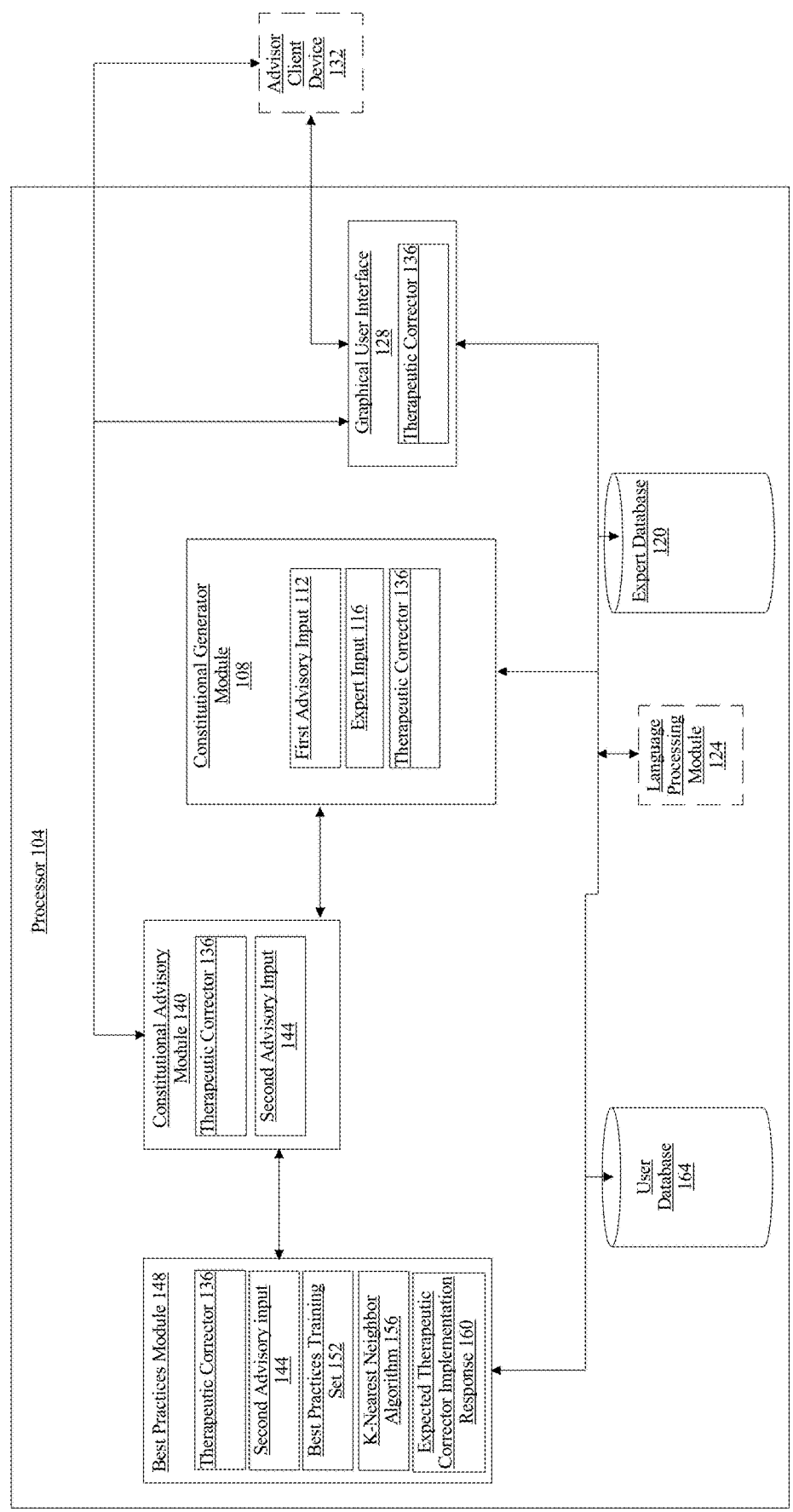
FIG. 1 is a block diagram illustrating an exemplary embodiment of a system for confirming an advisory interaction with an artificial intelligence platform.

Referring now to the drawings, FIG. 1 illustrates an exemplary embodiment of a system 100 for providing dynamic constitutional guidance. System 100 includes a processor. A processor 104 may include any computing device as described herein, including without limitation a microcontroller, microprocessor, digital signal processor 104 (DSP) and/or system on a chip (SoC) as described herein. A processor 104 may be housed with, may be incorporated in, or may incorporate one or more sensor of at least a sensor. Computing device may include, be included in, and/or communicate with a mobile device such as a mobile telephone or smartphone. A processor 104 may include a single computing device operating independently, or may include two or more computing device operating in concert, in parallel, sequentially or the like; two or more computing devices may be included together in a single computing device or in two or more computing devices. A processor 104 with one or more additional devices as described below in further detail via a network interface device. Network interface device may be utilized for connecting a processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. A processor 104 may include but is not limited to, for example, A processor 104 or cluster of computing devices in a first location and a second computing device or cluster of computing devices in a second location. A processor 104 may include one or more computing devices dedicated to data storage, security, distribution of traffic for load balancing, and the like. A processor 104 may distribute one or more computing tasks as described below across a plurality of computing devices of computing device, which may operate in parallel, in series, redundantly, or in any other manner used for distribution of tasks or memory between computing devices. A processor 104 may be implemented using a "shared nothing" architecture in which data is cached at the worker, in an embodiment, this may enable scalability of system 100 and/or computing device.

With continued reference to FIG. 1, a processor 104 may be designed and/or configured to perform any method, method step, or sequence of method steps in any embodiment described in this disclosure, in any order and with any degree of repetition. For instance, a processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A processor 104 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. A processor 104 may include one or more modules as illustrated herein which demonstrate how a particular system may operate. One or more modules as described in this disclosure may be configured to be implemented as any hardware and/or software module. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a constitutional generator module 108. Constitutional generator module 108 may be implemented as any hardware and/or software module. Constitutional generator module 108 is designed and configured to receive a first advisory input 112 containing a constitutional inquiry and a user identifier; retrieve an expert input 116 from an expert database 148 operating on the processor as a function of the first advisory input 112 and the user identifier; select a machine-learning model as a function of the expert input 116; and generate a therapeutic corrector 136 utilizing the machine-learning model and the advisory input wherein the therapeutic corrector 136 further comprises a response to the constitutional inquiry;

With continued reference to FIG. 1, constitutional generator module 108 is configured to receive a first advisory input 112 containing a constitutional inquiry and a user identifier from an advisor client device operated by an informed advisor. A "first advisory input" as used in this disclosure, includes any medical inquiry generated by an informed advisor. A "medical inquiry" as used in this disclosure, includes any question, input, or advice sought by an informed advisor of a medical nature. Medical nature includes the science and/or practice of the diagnosis, treatment, and prevention of disease. A "constitutional inquiry" as used in this disclosure, includes any inquiry pertaining to the human body. For instance and without limitation, a constitutional inquiry may include advice sought in regard to the best treatment for a user with an aggressive form of cancer. In yet another non-limiting example, a constitutional inquiry may include advice sought in regard to possible diagnoses for a user who complains of symptoms such as chills, body aches, fatigue, and lethargy. An informed advisor, as used in this disclosure, includes a person who is licensed by a state, federal, and/or international licensing agency that helps in identifying, preventing, and/or treating illness and/or disability. An informed advisor may include persons such as a functional medicine doctor, a doctor of osteopathy, a nurse practitioner, a physician assistant, a Doctor of Optometry, a Doctor of Dental Medicine, a Doctor of Dental Surgery, a naturopathic doctor, a Doctor of Physical Therapy, a nurse, a doctor of chiropractic medicine, a doctor of oriental medicine and the like. An informed advisor may include other skilled professionals such as nurses, respiratory therapists, pharmacists, home health aides, audiologists, clinical nurse specialists, nutritionists, dieticians, clinical psychologists, psychiatric mental health nurse practitioners, spiritual coaches, life coaches, holistic medicine specialists, acupuncturists, reiki masters, yoga instructors, holistic health coaches, wellness advisors and the like. An advisor client device may include any device as described below in more detail.

With continued reference to FIG. 1, a "user identifier' as used in this disclosure, includes any data that uniquely identifies a particular user. Data may include a user's name, a user's date of birth, a user's medical identification number, a public and/or private key pair, a cryptographic hash, a biometric identifier such as an iris scan, fingerprint scan, a palm vein scan, a retina scan, facial recognition, DNA, a personal identification number, a driver's license or passport, token-based identification systems, digital signatures, and the like. A user identifier may be an identifier that is unique as compared to any other user identifier within system 100. A user identifier may include a statistically ensured unique identifier such as a global unique identifier (GUID) or a universally unique identifier (UUID).

With continued reference to FIG. 1, constitutional generator module 108 is configured to retrieve an expert input 116 from an expert database operating on a processor 104. An "expert input," as used in this disclosure, includes any expert submission, such as a textual submission, expert paper, form entry or the like. An "expert" as used in this disclosure includes any health professional who may meet one or more criterion including for example obtaining board certification in a particular specialty, having clinical trial experience, being published in textbooks and peer-reviewed medical media, giving presentations at medical meetings, being involved in formulary committee participation, having a thriving clinical practice, affiliations with notation at a teaching institution, treating particular specialties and populations of patients, holding various positions or titles, having a diverse publication history such as prolific authorship, editorials, clinical guidelines and the like, having research experience and the like. A health professional includes any professional suitable for use as an informed advisor. For example, a health professional may include a functional medicine physician or a nurse practitioner who treats heart failure patients. An expert input 116 may include one or more data entries describing current treatment guidelines, best practices for treating a particular disease state, best machine-learning algorithms to generate a response to particular advisory inputs, best machine-learning models to use to generate a response to particular advisory inputs and the like. An expert input 116 may be received live and in real time. In yet another non-limiting example, an expert input 116 may be received at various times and one or more expert input 116 may be stored in an expert database which include any data structure as described in more detail below.

With continued reference to FIG. 1, expert input 116 may include temporal attributes, such as timestamps which may be utilized to select only expert input 116 more recently entered for training data and/or machine-learning model selection as described below in more details. Constitutional generator module 108 may receive an update to one or more expert input 116 and may perform one or more modifications to expert input 116. For example, a clinical trial may turn out to fail and as such constitutional generator module 108 may remove it from data, as a result. In yet another non-limiting example, a medical and/or academic paper, or a study on which it was based, may be revoked; and constitutional generator module 108 may remove it. Expert input 116 may be stored in one or more database structures on best practices module 148 operating on a processor 104.

With continued reference to FIG. 1, expert input 116 may be stored in an expert database 120 located within best practices module. Expert database 120 may be implemented, without limitation, as a relational database, a key-value retrieval datastore such as a NOSQL database, or any other format or structure for use as a datastore that a person skilled in the art would recognize as suitable upon review of the entirety of this disclosure. Expert input 116 may include textual data such as numerical, character, and/or string data. Textual data may include a standardized name and/or code for a disease, disorder, measurement, or the like; codes may include diagnostic codes and/or diagnosis codes, which may include without limitation codes in diagnosis classification systems such as The International Statistical Classification of Diseases and Related Health Problems (ICD). In general, there is no limitation on forms textual data or non-textual data used expert input 116 may take; persons skilled in the art, upon reviewing the entirety of this disclosure, will be aware of various forms which may be suitable for use as periodic longevity consistently with this disclosure.

With continued reference to FIG. 1, expert database 120 may store one or more expert input 116 as image data, such as for example, a computed tomography (CT) scan or a magnetic resonance image (MRI). Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, system 100 may include a language processing module 124. Language processing module 124 may be configured to extract one or more words from a first advisory input 112 and/or a user identifier and retrieve an expert input 116 based on advisory input and/or the user identifier. Language processing module 124 may include any hardware and/or software module. Language processing module 124 may be configured to extract, from one or more inputs, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

With continued reference to FIG. 1, language processing module 124 may operate to produce a language processing model. Language processing model may include a program automatically generated by a processor 104 and/or language processing module 124 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words describing and/or including constitutional data and/or ameliorative recommendation data may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given element of constitutional data and/or ameliorative recommendation data; positive or negative indication may include an indication that a given document is or is not indicating an element of constitutional data and/or ameliorative recommendation data. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory on a processor 104, or the like.

Still referring to FIG. 1, language processing module 124 and/or a processor 104 may generate a language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 124 may combine two or more approaches. For instance, and without limitation, machine-learning program may use a combination of Naïve-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 124 may use a corpus of documents to generate associations between language elements in a language processing module 124, and a processor 104 may then use such associations to analyze words extracted from one or more documents and determine that the one or more documents indicate significance of a category of physiological data, a given relationship of such categories to prognostic labels, and/or a given category of prognostic labels. In an embodiment, a processor 104 may perform this analysis using a selected set of significant documents, such as documents identified by one or more experts as representing good science, good clinical analysis, or the like; experts may identify or enter such documents via a graphical user interface 128 as described below, or may communicate identities of significant documents according to any other suitable method of electronic communication, or by providing such identity to other persons who may enter such identifications into a processor 104. Documents may be entered into a processor 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, a processor 104 may automatically obtain the document using such an identifier, for instance by submitting a request to a database or compendium of documents such as JSTOR as provided by Ithaka Harbors, Inc. of New York.

With continued reference to FIG. 1, system 100 may include a graphical user interface 128. Graphical user interface 128 may include without limitation a form or other graphical element having data entry fields, wherein one or more experts, including without limitation clinical and/or scientific experts, may enter information describing one or more expert input 116. Fields in graphical user interface 128 may provide options describing previously identified submissions including, for instance drop-down lists where experts may be able to select one or more entries to indicate their usefulness and/or significance in the opinion of the experts. Fields may include free-form entry fields such as text-entry fields where an expert may be able to type or otherwise enter text, enabling an expert to propose or suggest new or amended inputs not previously recorded. Graphical user interface 128 may include fields corresponding to machine-learning models, training sets, and/or machine-learning algorithms where an expert may view particular diagrams and/or pictures of any of the above. Graphical user interface 128 may allow for an expert to zoom in on a particular field or open a drop-down list in a new window to highlight more details. Graphical user interface 128 may include a field that allows an expert to indicate a reference to a particular document or journal article.

With continued reference to FIG. 1, one or more expert input 116 may be received from an advisor client device. Advisor client device 132 may include without limitation, a display in communication with a processor, where a display may include any display as described herein. Advisor client device 132 may include an additional computing device, such as a mobile device, laptop, desktop computer and the like. Advisor client device 132 may transmit one or more expert input 116 to processor 104 utilizing any network methodology as described herein. Advisor client device may be operated by an informed advisor. An informed advisor may include any of the informed advisors as described herein.

With continued reference to FIG. 1, constitutional generator module 108 is configured to select a machine-learning process as a function of an expert input 116. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

With continued reference to FIG. 1, supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of comprehensive diagnoses as inputs, priority treatments as outputs, and a scoring function representing a desired form of relationship to be detected between elements of comprehensive diagnoses and priority treatments; scoring function may, for instance, seek to maximize the probability that a given element of a comprehensive diagnosis is associated with a given priority treatment and/or combination of comprehensive diagnoses to minimize the probability that a given element of a comprehensive diagnosis and/or combination of elements comprehensive diagnoses are not associated with a given priority treatment and/or combination of priority treatments. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Persons skilled in the art, upon reviewing the entirety of this disclosure, will be aware of various possible variations of supervised machine-learning algorithms that may be used to determine relation between comprehensive diagnoses and priority treatments. In an embodiment, one or more supervised machine-learning algorithms may be restricted to a particular domain for instance, a supervised machine-learning process may be performed with respect to a given set of parameters and/or categories of parameters that have been suspected to be related to a given set of comprehensive diagnoses, and/or are specified as linked to a medical specialty and/or field of medicine covering a particular body system or medical specialty. As a non-limiting example, a particular set of diagnoses that indicate emergency medical conditions may be typically associated with a known urgency to seek medical attention and be treated, and a supervised machine-learning process may be performed to relate those comprehensive diagnoses to priority treatments; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate priority treatments. Additional supervised learning processes may be performed without domain restrictions to detect, for instance, previously unknown and/or unsuspected relationships between comprehensive diagnoses and priority treatments.

With continued reference to FIG. 1, "training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by a processor may correlate any input data as described in this disclosure to any output data as described in this disclosure.

With continued reference to FIG. 1, a machine-learning process may include an unsupervised machine-learning process. An unsupervised machine-learning process, as used herein, is a process that derives inferences in datasets without regard to labels; as a result, an unsupervised machine-learning process may be free to discover any structure, relationship, and/or correlation provided in the data. An unsupervised machine-learning process may include calculating one or more algorithms or equations including clustering algorithms such as hierarchical clustering, k-means clustering, mixture models, DBSCAN, OPTICS algorithm, and the like; anomaly detection such as local outlier factor; neural networks such as autoencoders, deep belief nets, Hebbian learning, generative adversarial networks, self-organizing map, and the like.

With continued reference to FIG. 1, a machine-learning process may include a lazy-learning process. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at generating a therapeutic corrector 136. As a non-limiting example, an initial heuristic may include a ranking of potential treatments according to relation to a test type of a first advisory input 112; ranking may include, without limitation, ranking according to significance scores of associations between of a first advisory input 112 and potential treatments, for instance as calculated as described above. Heuristic may include selecting some number of highest-ranking associations and/or potential treatments. Constitutional generator module 108 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate therapeutic corrector 136 outputs as described in this disclosure, including without limitation lazy learning applications of machine-learning algorithms as described in further detail below.

With continued reference to FIG. 1, unsupervised processes may be subjected to domain limitations. For instance, and without limitation, an unsupervised process may be performed regarding a comprehensive set of data regarding one person, such as demographic information including age, sex, race, geographical location, profession, and the like. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of dietary data, a group of people having a shared value for an element and/or category of demographic data; as illustrative examples, cohort could include all advisory inputs relating to diagnoses, all advisory inputs relating to treatments, all advisory inputs relating to suggested laboratory results or the like. Persons skilled in the art, upon reviewing the entirety of this disclosure, will be aware of a multiplicity of ways in which cohorts and/or other sets of data may be defined and/or limited for a particular unsupervised learning process.

With continued reference to FIG. 1, constitutional generator module 108 is configured to generate a therapeutic corrector 136 utilizing the machine-learning process and the advisory input. A "therapeutic corrector" as used in this disclosure, includes any response generated in response to an inquiry contained within a constitutional inquiry. A response may include a list of potential diagnoses, a list of available treatment options to try, a list of suggested lab work to analyze, and the like. For instance and without limitation, a therapeutic inquiry may contain a user's lab work showing elevate sodium levels and positive b-type natriuretic peptide and contain an inquiry looking for a list of potential diagnoses. Constitutional generator module 108 may utilize any machine-learning process as described above to generate a therapeutic corrector 136 that includes a list of potential diagnoses that includes heart failure, myocardial infarction, and chronic fatigue syndrome. In yet another non-limiting example, a therapeutic inquiry may contain an inquiry that includes a recommendation for potential lab results that a functional medicine physician should run for a user who complains of symptoms such as weight loss, fatigue, depression, and lack of concentration. Constitutional generator module 108 may utilize any machine-learning process as described above to generate a therapeutic corrector 136 that includes a list of suggested lab results that includes enzyme linked immunosorbent assay (ELISA) for Lyme disease, Vitamin D panel, and a complete thyroid panel. Generating a therapeutic corrector 136 may include receiving therapeutic training data from an expert database 120 wherein the therapeutic training data includes a plurality of data entries containing constitutional inquiries correlated to therapeutic corrector 136; and generating using a supervised machine-learning algorithm a therapeutic model that outputs a therapeutic corrector 136 utilizing the therapeutic training data and the advisory input containing the constitutional inquiry. Therapeutic training data may include any of the training data as described above. In an embodiment, an expert input 116 may be utilized to select a particular training data set based on a particular constitutional inquiry. Generating a therapeutic corrector 136 may include receiving a plurality of unclassified data entries from an expert database 120; and generating using an unsupervised machine-learning algorithm an unsupervised model that outputs a therapeutic corrector 136 utilizing the plurality of unclassified data entries and the advisory input containing the constitutional inquiry.

With continued reference to FIG. 1, system 100 includes a constitutional advisory module 140. A constitutional advisory module 140 may be implemented as any hardware and/or data structure. A constitutional advisory module 140 is designed and configured to receive the therapeutic corrector 136 from the constitutional generator module 108; display the therapeutic corrector 136 on a graphical user interface 128 located on the processor; and receive a second advisory input 144 from an advisor client device operated by an informed advisor wherein the second advisory input contains a therapeutic corrector implementation response.

With continued reference to FIG. 1, a "second advisory input 144" as used in this disclosure, includes any input generated by an informed advisor in response to a therapeutic corrector 136. A second advisory input 144 includes a therapeutic corrector implementation response. A "therapeutic corrector implementation response" as used in this disclosure, includes any description that describes an informed advisor's experience with implementing or not implementing a particular therapeutic corrector 136. Implementation may include any effort that an informed advisor may put forth in regard to utilizing a particular therapeutic corrector 136 in the informed advisor's clinical practice and in reference to the particular user that the therapeutic corrector 136 was generated in reference to. A therapeutic implementation response may contain a description that describes how much or how little an informed advisor implemented a particular therapeutic corrector 136 and may also describe whether the therapeutic corrector 136 ultimately helped the user. A therapeutic implementation response may contain a description of one or more results an informed advisor noticed based on implementing a particular therapeutic corrector. Results may include side effects, changes in lab values, subsequently generated diagnoses, elimination of one or more diagnoses, addition of one or more diagnoses, additional tests performed, additional clinical lab work performed and the like. For instance and without limitation, an informed advisor may generate a therapeutic corrector implementation response in reference to a therapeutic corrector 136 that contained a list of suggested laboratory tests to consider in order to help diagnose a user with mysterious symptoms. In such an instance, the informed advisor may generate a therapeutic corrector implementation response that contains a description of which of the suggested laboratory tests the informed advisor performed and if any aided the informed advisor in determining a diagnosis for the user. In yet another non-limiting example, an informed advisor may generate a therapeutic corrector implementation response in reference to a therapeutic corrector 136 that contained a list of two suggested treatment options to consider for a user that the informed advisor had diagnosed as having advanced multiple sclerosis. In such an instance, an informed advisor may generate a therapeutic corrector implementation response that contains a description of the user's experience with trying the two suggested treatment options and if either of the two treatment options helped slow the progression of the advanced multiple sclerosis. A therapeutic corrector implementation response may contain a description that details that the informed advisor chooses not to implement any of the suggested therapeutic corrector 136.

With continued reference to FIG. 1, constitutional advisory module 140 may be configured to authenticate advisory inputs. Constitutional advisory module 140 may receive in conjunction with a therapeutic corrector implementation response a first expert credential validator. A "first expert credential validator" as used in this disclosure, includes any unique identifier that validates a particular user as being an expert. A unique identifier may include an identifier that is unique to system 100, such as a series of numbers and/or letters. A unique identifier may include one or more licensing credentials such as a national provider identifier (NPI), a drug enforcement agency (DEA) number, an institutional provider identifier, a state licensing credential, and the like. Constitutional advisory module 140 may compare the first expert credential validator to a list of known expert credentials stored in an expert database 120. A list of known expert credentials may include a list of all known experts and expert credentials stored within expert database 120. A list of known expert credentials may be updated in live time to account for experts who may have one or more credentials taken away for misconduct, expire, lapse, gain new credentials and the like. Constitutional advisory module 140 determines that the first expert credential validator is authentic by confirming that the first expert credential validator is contained within the list of known expert credentials. Constitutional advisory module 140 authenticates the first advisory input 112 as a function of determining that the first expert credential validator is authentic.

With continued reference to FIG. 1, system 100 includes a best practices module 148. Best practices module 148 may be implemented as any hardware and/or software module. Best practices module 148 the best practices module 148 designed and configured to receive the second advisory input 144 containing the therapeutic corrector implementation response from the constitutional advisory module 140; receive the therapeutic corrector 136 from the constitutional generator module 108; retrieve from an expert database 120 located on the processor a best practices training set 152 wherein the best practices training set 152 correlates a therapeutic corrector 136 to therapeutic corrector implementation responses; calculate an optimal vector output for the therapeutic corrector 136 received from the constitutional generator module 108; generate an optimal vector output containing an expected therapeutic corrector implementation response 160; authenticate the advisory input containing the therapeutic corrector implementation response as a function of the expected therapeutic corrector implementation response 160; and update the best practices module 148 as a function of authenticating the second advisory input 144 containing the therapeutic corrector implementation response to the expected therapeutic corrector implementation response 160.

With continued reference to FIG. 1, best practices training set 152 may implemented as any training data as described above. Best practices training set 152 may include a plurality of data entries correlating a therapeutic corrector 136 to a therapeutic corrector implementation response. For instance and without limitation, best practices training set 152 may correlate a therapeutic corrector 136 such as implementation of low dose naltrexone (LDN) for chronic fatigue syndrome to a therapeutic corrector implementation response that includes increased energy, decreased fatigue, and greater ability to concentrate. In yet another non-limiting example, best practices training set 152 may correlate a therapeutic corrector 136 such as a diagnosis of rheumatoid arthritis to contain a therapeutic corrector implementation response that includes decreased joint pain, and better ability to exercise.

With continued reference to FIG. 1, best practices module 148 is configured to calculate an optimal vector output for the therapeutic corrector 136 utilizing a k-nearest neighbor algorithm 156 and best practices training set 152. "Optimal vector output" as used in this disclosure, includes a "first guess" by best practices module 148 at the nearest vector in the feature space containing an expected therapeutic corrector implementation response 160. An "expected therapeutic corrector implementation response 160" as used in this disclosure, includes any probable or predictable response to implementing a particular therapeutic corrector 136. Probable or predictable response may be known based on currently available medical literature, case studies, journal articles, expert input, data aggregations from surveyed responses, and the like. For instance and without limitation, a therapeutic corrector 136 such as initiating a fitness regimen may be related to an expected therapeutic corrector implementation response 160 such as weight loss. A therapeutic corrector 136 may be related to one or more expected therapeutic corrector implementation response 160. For instance and without limitation, a therapeutic corrector 136 such as diagnosis of generalized anxiety disorder may be related to one or more expected therapeutic corrector implementation response 160 that include decreased number of anxiety attacks, increased sleep, decreased chest pain, decreased anxiety caused by receiving a medical diagnosis, increased confidence, and the like. In yet another non-limiting example, a therapeutic corrector 136 such as a series of suggested lab panels and medical tests may be related to one or more expected therapeutic corrector implementation response 160 that include absence or presence of expected results, further lab tests or medical tests that were ordered, a potential diagnosis generated based on the suggested lab panels, and the like. K-nearest neighbor algorithm 156 may return a single matching entry or a plurality of matching entries. When a plurality of matching entries is returned, best practices module 148 may derive optimal vector from plurality of matching entries by aggregating matching entries; aggregation may be performed using any suitable method for aggregation, including component-wise addition followed by normalization, component-wise calculation of arithmetic means, or the like. "K-nearest neighbor algorithm 156" as used in this disclosure, includes a lazy-learning method that utilizes feature similarity to analyze how closely out-of-sample-features resemble training data to locate possible optimal vector output, classify possible optimal vector output, calculate an optimal vector output, and generate an optimal vector output. Calculating an optimal vector output utilizing a k-nearest neighbor algorithm 156 may include specifying a K-value, selecting k entries in a database which are closest to the known sample, determining the most common classifier of the entries in the database, and classifying the known sample. A lazy-learning process and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, best practices module 148 authenticates an advisory input containing a therapeutic corrector implementation response as a function of the expected therapeutic corrector implementation response 160. Best practices module 148 may compare a therapeutic corrector implementation response to one or more expected therapeutic corrector implementation response 160 to determine if the therapeutic corrector implementation response matches one or more expected therapeutic corrector implementation response 160. A therapeutic corrector implementation response that does not match one or more expected therapeutic corrector implementation response 160 may require further investigation and authentication. In such an instance, best practices module 148 may authenticate an advisory input containing a therapeutic corrector implementation response that does not match an expected therapeutic corrector implementation response 160 by obtaining a second opinion from a second informed advisor. Best practices module 148 may display the advisory input containing the therapeutic corrector implementation response and the expected therapeutic corrector implementation response 160 on a graphical user interface 128 located on the processor to a second informed advisor. A second informed advisor may include any other informed advisor other than a first informed advisor. A second informed advisor may include an expert in a particular field or specialty that may be related to a particular therapeutic corrector 136. In an embodiment, an informed advisor's area of expertise or specialty may be contained within expert database 120 and may be stored on list of experts. Best practices module 148 receives a second expected therapeutic corrector implementation response 160 from the second informed advisor. A "second expected therapeutic corrector implementation response 160" as used in this disclosure, includes any response suitable for use as first expected therapeutic corrector implementation response 160. A second expected therapeutic corrector implementation response 160 may be generated by an informed advisor who may be an expert or specialist in a particular field, specialty, and/or sub-specialty of medicine. In an embodiment, a second expected therapeutic corrector implementation response 160 may contain a response that may authenticate or not authenticate a response contained within a therapeutic corrector implementation response. For example, a therapeutic corrector implementation response may contain a description of testing for heavy metals in a user that showed user had high levels of cadmium which a first informed advisor attributed to excessive cigarette smoking by the user. A second expected therapeutic corrector implementation response 160 generated by a second informed advisor who may be a specialist in the field of toxicology may authenticate cadmium toxicity due to excessive cigarette smoking when an expected therapeutic implementation response does not contain cadmium toxicity due to cigarette smoking. Best practices module 148 may authenticate a second informed advisor's credentials and expertise in a fashion similar to authenticating a first informed advisor's credentials. Best practices module 148 may receive a second expert credential validator. Second expert credential validator may include any expert credential validator suitable for use as first expert credential validator. Best practices module 148 may compare the second expert credential validator to a list of known expert credentials storied in the expert database 120. Best practices module 148 may determine that the second expert credential validator is authentic and authenticate the second advisory input 144 as a function of determining that the second expert credential validator is authentic.

With continued reference to FIG. 1, best practices module 148 may authenticate an advisory input containing a therapeutic implementation response utilizing an expert periodical submission. An "expert periodical submission" as used in this disclosure, includes any publication written by one or more experts. A publication may include a journal article, clinical trial results, clinical trial data, a news article, a review, academic articles, scholarly articles and the like. Best practices module 148 may retrieve an expert periodical submission contained within the expert database 120. Best practices module 148 may locate an expected therapeutic corrector implementation response 160 contained within an expert periodical. For example, a particular journal article may describe an n of 1 study where an informed advisor observed a particular reaction to a medication only given to one user. Best practices module 148 may located this expected therapeutic corrector implementation response 160 contained within the journal article and compare it to a therapeutic corrector implementation response received from a first informed advisor who may have observed the same reaction to the medication. In an embodiment, expert periodical submissions may be organized within a best practices module 148 by topic to allow for easy searching and indexing to find expert periodical submissions that may pertain to a particular therapeutic corrector implementation response. Best practices module 148 may confirm the legitimacy of the first therapeutic implementation response when it finds the first therapeutic implementation response in an expert periodical submission located within expert database 120. Best practices module 148 may authenticate an advisory input by evaluating a user response to a particular therapeutic corrector 136. Best practices module 148 may retrieve an element of user constitutional data from a user database 164. "User constitutional data" as used in this disclosure, includes any data describing any health process and/or health measurement of a user. A health process may include any treatment prescribed for a user. Treatments may include any ameliorative process including prescription medications, medical procedures, medical tests, medical diagnostics, nutraceuticals, supplements, homeopathic remedies, exercise regimen, fitness routine, yoga practice, meditation sequence, relaxation techniques and the like. A health measurement may include any physically extracted sample which includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. User constitutional data may include one or more user generated responses detailing how a user feels after implementing a particular health process and/or having a particular health measurement analyzed. One or more user generated responses may be stored in a user database 164. User database 164 may be implemented as any data structure suitable for use as expert database 120 as described above. A user generated response may contain a description of how a user feels after implementing a particular meditation sequence and if the meditation sequence is helping treatment a particular ailment. Best practices module 148 may retrieve a particular element of user constitutional data and compare the element of user constitutional data to a therapeutic corrector implementation response. Best practices module 148 may then authenticate a first therapeutic implementation response utilizing an element of user constitutional data. For example, an element of user constitutional data that describes a user response to a medication as improving the user's fatigue may be utilized to authenticate a first therapeutic implementation response that contains a description of decreased fatigue from the medication user was taking which was a previously unreported side effect of the medication. In yet another non-limiting example, an element of user constitutional data that contains a user's chem-7 panel may be utilized to authenticate a first therapeutic implementation response that contains a description of increased serum sodium levels observed during exercise. In such an instance, best practices module 148 may evaluate a user's serum sodium level collected during exercise to confirm that it was increased. This may be performed when other methods of authentication are not available such as when increased serum sodium levels are not found in any expert periodical submissions or are unable to be authenticated by a second informed advisor.

With continued reference to FIG. 1, best practices module 148 updates the best practices module 148 as a function of authenticating the first advisory input 112 containing the therapeutic corrector implementation response. Updating the best practices module 148 may include incorporating a therapeutic corrector implementation response and/or a therapeutic corrector 136 into the best practices module 148 and/or expert database 120. For example, best practices module 148 may incorporate the therapeutic corrector 136 and the therapeutic corrector implementation response into a best practice training set 152. Updating the best practices module 148 may include incorporating the machine-learning model into the best practices module 148. A second advisory input 144 containing a therapeutic corrector implementation response that does not get authenticated may not be updated into the best practices module 148 so that non-authenticated responses are not utilized to generate subsequent responses within system 100. Instead, non-authenticated responses may be discarded and may not be incorporating into the best practices module 148.

Figure 2:
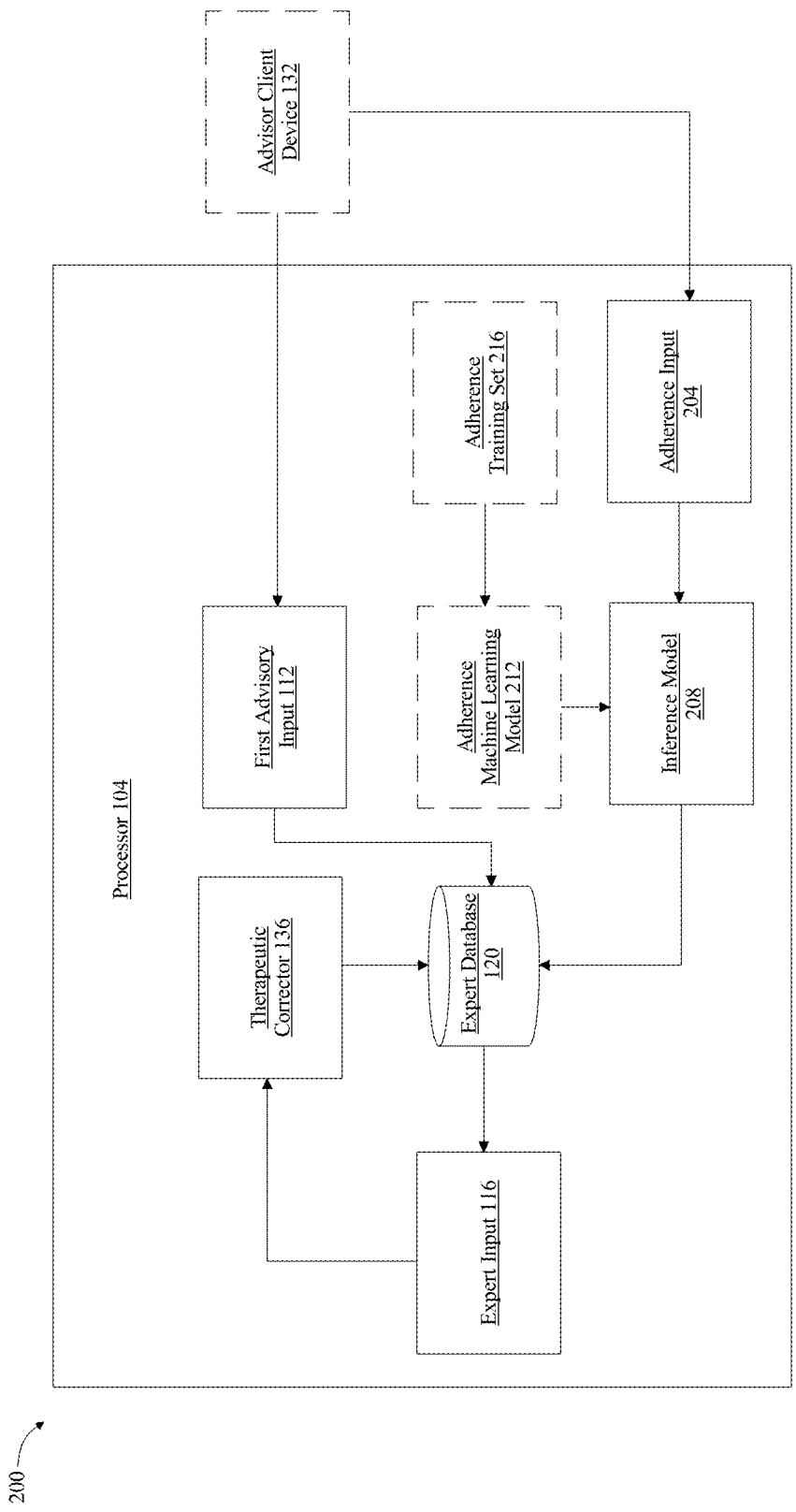
FIG. 2 is a block diagram illustrating an exemplary embodiment of an inference model.

Referring now to FIG. 2, an exemplary embodiment 200 of an inference model is illustrated. Processor 104 may be configured to obtain an adherence input 204 from advisor client device 132. As used in this disclosure an "adherence input" is an input that represents a user's adherence to therapeutic corrector 136. For example, and without limitation, first therapeutic corrector 136 of 7 days of exercise may relate to adherence input 204 of 4 days. Additionally or alternatively, adherence input 204 may include a quantitative value associated with the therapeutic corrector 136. For example, and without limitation, adherence input may be 22, wherein 22 represents a percentage of completion for therapeutic corrector 136. As a further non-limiting example, adherence input 204 may include a quantitative value of 6 for the number of completed tasks that therapeutic corrector 136 generated. Adherence input 204 may relate to one or more monitoring devices that are capable of monitoring a user's physiological data. As used in this disclosure "monitoring device" is an electronic device that is worn on the person of a user, such as without limitation close to and/or on the surface of the skin, wherein the device can detect, analyze, and transmit biochemical information concerning an individual. Monitoring device may include, without limitation, any device that further collects, stores, and analyzes data associated with adherence input 204. Monitoring device my consist of, without limitation, near-body electronics, on-body electronics, in-body electronics, electronic textiles, smart watches, smart glasses, smart clothing, fitness trackers, body sensors, wearable cameras, head-mounted displays, body worn cameras, Bluetooth headsets, wristbands, smart garments, chest straps, sports watches, fitness monitors, and the like thereof. Monitoring device may include, without limitation, earphones, earbuds, headsets, bras, suits, jackets, trousers, shirts, pants, socks, bracelets, necklaces, brooches, rings, jewelry, AR HMDs, VR HMDs, exoskeletons, location trackers, and gesture control wearables.

Still referring to FIG. 2, processor 104 may be configured to obtain adherence input 204 by determining a therapeutic effect as a function of therapeutic corrector 136. As used in this disclosure a "therapeutic effect" is the physiological response of the user's body due to therapeutic corrector 136. As a non-limiting example a therapeutic response of reduced inflammation in a particular organ and/or tissue as a result of a therapeutic corrector associated with antioxidants. As a further non-limiting example, a therapeutic response of increased catabolic function may be a result of a therapeutic corrector associated with increased piperine. Therapeutic effect may be determined by establishing a therapeutic enumeration. As used in this disclosure a "therapeutic enumeration" is a measurable value associated with a user's symptoms. As a non-limiting example, a therapeutic enumeration of 23 may be identified for a user's elevated levels of saturated fats. As a further non-limiting example, a therapeutic enumeration of 7 may be identified as a function of a decreased caloric expenditure. Therapeutic effect may be determined by distinguishing a therapeutic divergence. As used in this disclosure a "therapeutic divergence" is a measurable value comprising the magnitude of divergence of therapeutic enumeration and a therapeutic recommendation. As used in this disclosure a "therapeutic recommendation" is a recommendation and/or guideline associated with the user's symptoms. As a non-limiting example, therapeutic recommendation recommend that a user produces 1.42 Liters and/or 1.5 quarts of mucus per day, wherein a therapeutic divergence may be 2 for a user that produces 3.87 Liters and/or 4.09 quarts of mucus per day. Therapeutic effect may be determined as a function of therapeutic enumeration, therapeutic divergence, and a therapeutic threshold. As used in this disclosure a "therapeutic threshold" is an upper and/or lower limit that a therapeutic divergence should not diverge from. For example, and without limitation, therapeutic threshold may include an upper limit of 8, wherein a lower limit is 3, for a therapeutic divergence associated with $O_2$ saturation. As a further non-limiting example, therapeutic threshold may include an upper limit of 23, wherein a lower limit is 13, for a therapeutic divergence associated with bacterial presence in the blood.

Still referring to FIG. 2, processor 104 is configured to calculate an inference model 208. As used in this disclosure an "inference model" is an algorithm and/or function that produces associations between one or more adherence inputs such that a prediction and/or estimation of the next user's symptoms and or progression. As a non-limiting example, inference model 208 may include an algorithm for the prediction of a particular symptom and/or illness. For example, and without limitation, therapeutic corrector 136 may identify a treatment for COVID-19, wherein inference model 208 may be calculated to predict the next symptoms and/or therapeutic correctors that the user may require. Inference model 208 may be calculated as a function of an adherence machine-learning model 212. As used in this disclosure "adherence machine-learning model" is a machine-learning model to produce an inference model given adherence inputs as inputs; this is in contrast to a non-machine learning software program where the commands to be executed are determined in advance by a user and written in a programming language. Adherence machine-learning model 212 may include one or more adherence machine-learning processes such as supervised, unsupervised, or reinforcement machine-learning processes that processor 104 and/or a remote device may or may not use in the determination of inference model 208. As used in this disclosure "remote device" is an external device to processor 104. An adherence machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, processor 104 may train adherence machine-learning model 212 as a function of an adherence training set 216. As used in this disclosure "adherence training set" is a training set that correlates a monitoring element and/or a therapeutic corrector to an inference model. As used in this disclosure a "monitoring element" is an element of datum that is identified as a function of a monitoring device, wherein a monitoring device is described above in detail. For example, and without limitation, a monitoring element of elevated heart rate and a therapeutic corrector of a reduced heart rate may relate to an inference model that calculates the predicted next symptoms and/or effects. Adherence training set 216 may be received as a function of user-entered valuations of monitoring elements, therapeutic correctors, and/or inference models. Processor 104 may receive adherence training set by receiving correlations of monitoring elements and/or therapeutic correctors that were previously received and/or determined during a previous iteration of calculating inference model 208. Adherence training set 216 may be received by one or more remote devices that at least correlate a monitoring element and/or therapeutic corrector to an inference model, wherein a remote device is an external device to processor 104, as described above. Adherence training set may be received in the form of one or more user-entered correlations of a monitoring element and/or therapeutic corrector to an inference model.

Still referring to FIG. 2, processor 104 may receive adherence machine-learning model 212 from a remote device that utilizes one or more adherence machine learning processes, wherein a remote device is described above in detail. For example, and without limitation, a remote device may include a computing device, external device, processor, and the like thereof. Remote device may perform the adherence machine-learning process using the adherence training set to generate inference model 208 and transmit the output to processor 104. Remote device may transmit a signal, bit, datum, or parameter to processor 104 that at least relates to inference model 208. Additionally or alternatively, the remote device may provide an updated machine-learning model. For example, and without limitation, an updated machine-learning model may be comprised of a firmware update, a software update, an adherence machine-learning process correction, and the like thereof. As a non-limiting example a software update may incorporate a new monitoring element that relates to a modified therapeutic corrector. Additionally or alternatively, the updated machine learning model may be transmitted to the remote device, wherein the remote device may replace the adherence machine-learning model with the updated machine-learning model and calculate the inference model as a function of the monitoring using the updated machine-learning model. The updated machine-learning model may be transmitted by the remote device and received by processor 104 as a software update, firmware update, or corrected adherence machine-learning model. For example, and without limitation adherence machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 2, processor 104 may calculate inference model 208 by generating a physiological progression parameter. As used in this disclosure a "physiological progression parameter" is a parameter associated with the overall timeline of a user's symptoms. For example, a user's symptoms may include a common cold, wherein a user may be on day 4 of the common cold, wherein it takes 8 days for the common cold to be eliminated. Additionally or alternatively, physiological progression parameter may include determining a percentage of elimination of a user's symptoms, wherein the percentage denotes the total amount of time with the symptoms and the total amount of time remaining. As a non-limiting example, a percentage of 22% may be identified for a user that is 22% completed with the symptoms and/or ailments. Physiological progression parameter may include determining the pace at which the symptoms and/or ailments are progressing. For example, and without limitation, physiological progression parameter may identify that a user's symptoms are progressing slowly and/or rapidly. Physiological progression parameter may be generated by identifying a status of therapeutic corrector 136. As user in this disclosure a "status" is a current state of a user's symptoms and/or therapeutic corrector 136 at a time period, wherein a time period includes seconds, minutes, hours, days, weeks, months, years, and the like thereof. Processor 104 may determine functional checkpoints as a function of therapeutic corrector 136. As used in this disclosure a "functional checkpoint" is a barrier and/or marker that is identified in therapeutic corrector 136 that represents a significant point in the physiologic process. As a non-limiting example, functional checkpoint may include a significant point associated with eliminating a cough and/or sneeze as a function of therapeutic corrector 136. As a further non-limiting example, functional checkpoint may include a significant point associated with a particular quantity and/or concentration of a biomarker in a user's body, wherein a "biomarker," as used herein, is a molecule and/or chemical that identifies the health status of a user's body. Processor 104 generates physiological progression parameter as a function of functional checkpoint to at least determine the location and or progress of a user's symptoms in relation to the ailment.

Still referring to FIG. 2, processor 104 updates expert database 120 as a function of inference model 208 and therapeutic corrector 136. Updating expert database 120 may be conducted similarly to FIG. 1. Processor 104 may update expert database 120 by generating a therapeutic framework. As used in this disclosure a "therapeutic framework" is a framework of programs, compilers, code, libraries, application programming interfaces, and/or data associated with therapeutic correctors and/or inference models. As a non-limiting example, therapeutic framework may include one or more decision support systems, web frameworks, cactus frameworks, and the like thereof. Information in therapeutic frame representing the generated therapeutic corrector and/or the calculated inference model may be collected, stored, and distributed. As a non-limiting example, therapeutic framework may be accessed by one or more advisors in one or more geographical locations. As a further non-limiting example, therapeutic framework may collect and store a plurality of inference models for a therapeutic corrector and/or a plurality of therapeutic corrects for an inference model. Therapeutic framework may be generated as a function of producing a cryptographic identifier. As used in this disclosure a "cryptographic identifier" is data that is obtained as user identifier data that is cryptographically altered and/or secured. In an embodiment and without limitation, cryptographic identifier prevents user identifier from being accessed on therapeutic framework, such that only therapeutic corrector and/or inference models are presented on therapeutic framework.

Still referring to FIG. 2, cryptographic identifier may include data that has been converted by a cryptographic system. In one embodiment, a cryptographic system is a system that converts data from a first form, known as "plaintext," which is intelligible when viewed in its intended format, into a second form, known as "ciphertext," which is not intelligible when viewed in the same way. Ciphertext may be unintelligible in any format unless first converted back to plaintext. In one embodiment, a process of converting plaintext into ciphertext is known as "encryption." Encryption process may involve the use of a datum, known as an "encryption key," to alter plaintext. Cryptographic system may also convert ciphertext back into plaintext, which is a process known as "decryption." Decryption process may involve the use of a datum, known as a "decryption key," to return the ciphertext to its original plaintext form. In embodiments of cryptographic systems that are "symmetric," decryption key is essentially the same as encryption key: possession of either key makes it possible to deduce the other key quickly without further secret knowledge. Encryption and decryption keys in symmetric cryptographic systems may be kept secret and shared only with persons or entities that the user of the cryptographic system wishes to be able to decrypt the ciphertext. One example of a symmetric cryptographic system is the Advanced Encryption Standard ("AES"), which arranges plaintext into matrices and then modifies the matrices through repeated permutations and arithmetic operations with an encryption key.

In embodiments of cryptographic systems that are "asymmetric," either encryption or decryption key cannot be readily deduced without additional secret knowledge, even given the possession of a corresponding decryption or encryption key, respectively; a common example is a "public key cryptographic system," in which possession of the encryption key does not make it practically feasible to deduce the decryption key, so that the encryption key may safely be made available to the public. An example of a public key cryptographic system is RSA, in which an encryption key involves the use of numbers that are products of very large prime numbers, but a decryption key involves the use of those very large prime numbers, such that deducing the decryption key from the encryption key requires the practically infeasible task of computing the prime factors of a number which is the product of two very large prime numbers. Another example is elliptic curve cryptography, which relies on the fact that given two points P and Q on an elliptic curve over a finite field, and a definition for addition where A+B=R, the point where a line connecting point A and point B intersects the elliptic curve, where "0," the identity, is a point at infinity in a projective plane containing the elliptic curve, finding a number k such that adding P to itself k times results in Q is computationally impractical, given correctly selected elliptic curve, finite field, and P and Q.

Figure 3:
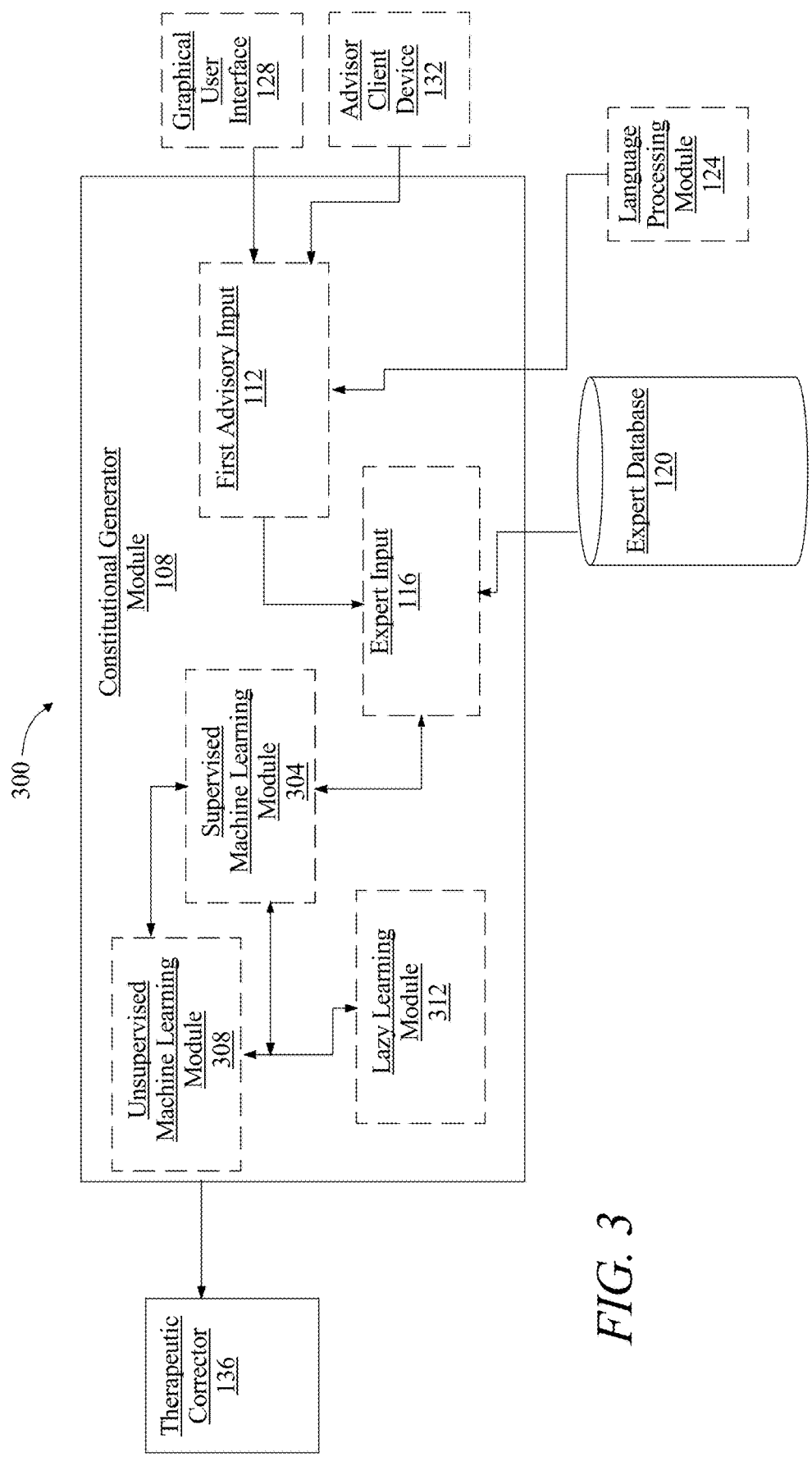
FIG. 3 is a block diagram illustrating an exemplary embodiment of a constitutional generator module.

Referring now to FIG. 3, an exemplary embodiment 300 of constitutional generator module 108 is illustrated. Constitutional generator module 108 may be implemented as any hardware and/or software module. Constitutional generator module 108 receives a first advisory input 112 containing a constitutional inquiry and a user identifier. Constitutional generator module 108 may receive a first advisory input 112 from an input generated on graphical user interface 128. Constitutional generator module 108 may receive a first advisory input 112 from an input generated from an advisor client device. First advisory input 112 containing a constitutional inquiry may include any of the first advisory input 112 as described above in more detail in reference to FIG. 1. For example, first advisory input 112 may include a list of symptoms that a user may be experiencing and contain a request for a potential diagnosis. In yet another non-limiting example, first advisory input 112 may include a description of a series of symptoms that a user may be experiencing with a request to understand what tests an informed advisor should run to confirm or rule out potential diagnoses. In yet another non-limiting example, first advisory input 112 may include a question as to what tests an informed advisor should run to check progression of disease state such as small intestinal bacterial overgrowth (SIBO), which the informed advisor may be unfamiliar with treating.

With continued reference to FIG. 3, constitutional generator module 108 retrieves an expert input 116 from expert database 120 as a function of a first advisory input 112 and a user identifier. Expert input 116 may include any of the expert input 116 as described above in reference to FIG. 1. Expert input 116 may include an indication as to what machine-learning process constitutional generator module 108 may utilize to generate a therapeutic corrector 136 for a particular first advisory input 112. Constitutional generator module 108 may utilize language processing module 124 to extract one or more keywords contained within a first advisory input 112. For example, language processing module 124 may extract a string of words from a particular first advisory input 112 that contain a request for a potential diagnosis for a user who complains of symptoms that include fever, chills, and diarrhea. In such an instance, constitutional generator module 108 may utilize the string of words that contain user's symptoms to retrieve an expert input 116 that contains suggested training sets and/or machine-learning models that may be best to utilize with user's symptoms to generate a therapeutic corrector 136. In yet another non-limiting example, constitutional generator module 108 may utilize language processing module 124 to extract a particular diagnosis contained within a first advisory input 112 that may be utilized by constitutional generator module 108 to select an expert input 116 that contains suggested training sets that may be utilized to select a machine-learning process such as a supervised machine-learning model to output a therapeutic corrector 136 that contains suggested treatment options for the particular diagnosis contained within the first advisory input 112. Constitutional generator module 108 may utilize a user identifier to select an expert input 116 such as by utilizing a user identifier to review previous machine-learning models that were utilized to generate previous therapeutic corrector 136 for a user.

With continued reference to FIG. 3, constitutional generator module 108 may include supervised machine-learning module 304. Supervised machine-learning module 304 may be implemented as any hardware and/or software module. Supervised machine-learning module 304 may be configured to receive therapeutic training data from expert database 120. Therapeutic training data includes a plurality of data entries containing constitutional inquiries correlated to therapeutic corrector 136. For instance and without limitation, therapeutic training data may include constitutional inquiries that contain a list of symptoms correlated to therapeutic corrector 136 that contain potential diagnoses. One or more training sets may be stored in expert database 120. Therapeutic training data may be generated based on expert input 116, including any of the expert input 116 as described above. Supervised machine-learning module 304 may generate using a supervised machine-learning algorithm a therapeutic model that outputs a therapeutic corrector 136 utilizing the therapeutic training data and the advisory input containing the constitutional inquiry. Therapeutic model may include any machine learning process and may include linear or polynomial regression algorithms. Therapeutic model may include one or more equations. Therapeutic model may include a set of instructions utilized to generate outputs based on inputs derived using a machine-learning algorithm and the like. Therapeutic model may be utilized to generate a therapeutic corrector 136 that contains a response to a constitutional inquiry.

With continued reference to FIG. 3, constitutional generator module 108 may include unsupervised machine-learning module 308. Unsupervised machine-learning module may be implemented as any hardware and/or software module. Unsupervised machine-learning module may be configured to receive a plurality of unclassified data entries from expert database 120. "Unclassified data entries" as used in this disclosure, includes one or more data entries that have not been utilized in combination with one or more classification algorithms to generate one or more classification labels. Classification algorithms include any of the classification algorithms as described above including logistic regression, Naïve Bayes, decision trees, k-nearest neighbors, and the like. A "classification label" as used in this disclosure, includes any identification as to whether a particular data entries or series of data entries belong to a class or not. Classification may include the process of assigning a set of predefined categories or classes to one or more data entries utilizing classification algorithms. Predefined categories or classes may be generated and/or selected based on expert input 116, such as from expert database 120. Unsupervised machine-learning module may generate using an unsupervised machine-learning algorithm an unsupervised model that outputs a therapeutic correcting utilizing the plurality of unclassified data entries and the advisory input containing the constitutional inquiry. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, unsupervised machine-learning module 308 may perform an unsupervised machine learning process on plurality of unclassified data entries, which may cluster data contained within plurality of unclassified data entries according to detected relationships between elements of unclassified data entries, including without limitation correlations of elements of advisory inputs to each other and correlations of therapeutic corrector 136 to each other; such relations may then be combined with supervised machine learning results to add new criteria for supervised machine-learning module 304 to apply in relating advisory inputs to therapeutic corrector 136.

With continued reference to FIG. 3, constitutional generator module 108 may include lazy learning module 312. Lazy learning module may be implemented as any hardware and/or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a therapeutic corrector 136 associated with advisory inputs, using therapeutic training data. As a non-limiting example, an initial heuristic may include a ranking of therapeutic corrector 136 according to relation to a test type of an advisory input, one or more categories of therapeutic corrector 136 identified in test type of an advisory input, and/or one or more values detected in an advisory input; ranking may include, without limitation, ranking according to significance scores of associations between elements of advisory inputs and therapeutic corrector 136, for instance as calculated as described above. Heuristic may include selecting some number of highest-ranking associations and/or therapeutic corrector 136. Lazy learning module may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate therapeutic corrector 136 as described in this disclosure, including without limitation lazy learning applications of machine-learning algorithms as described in further detail below.

Figure 4:
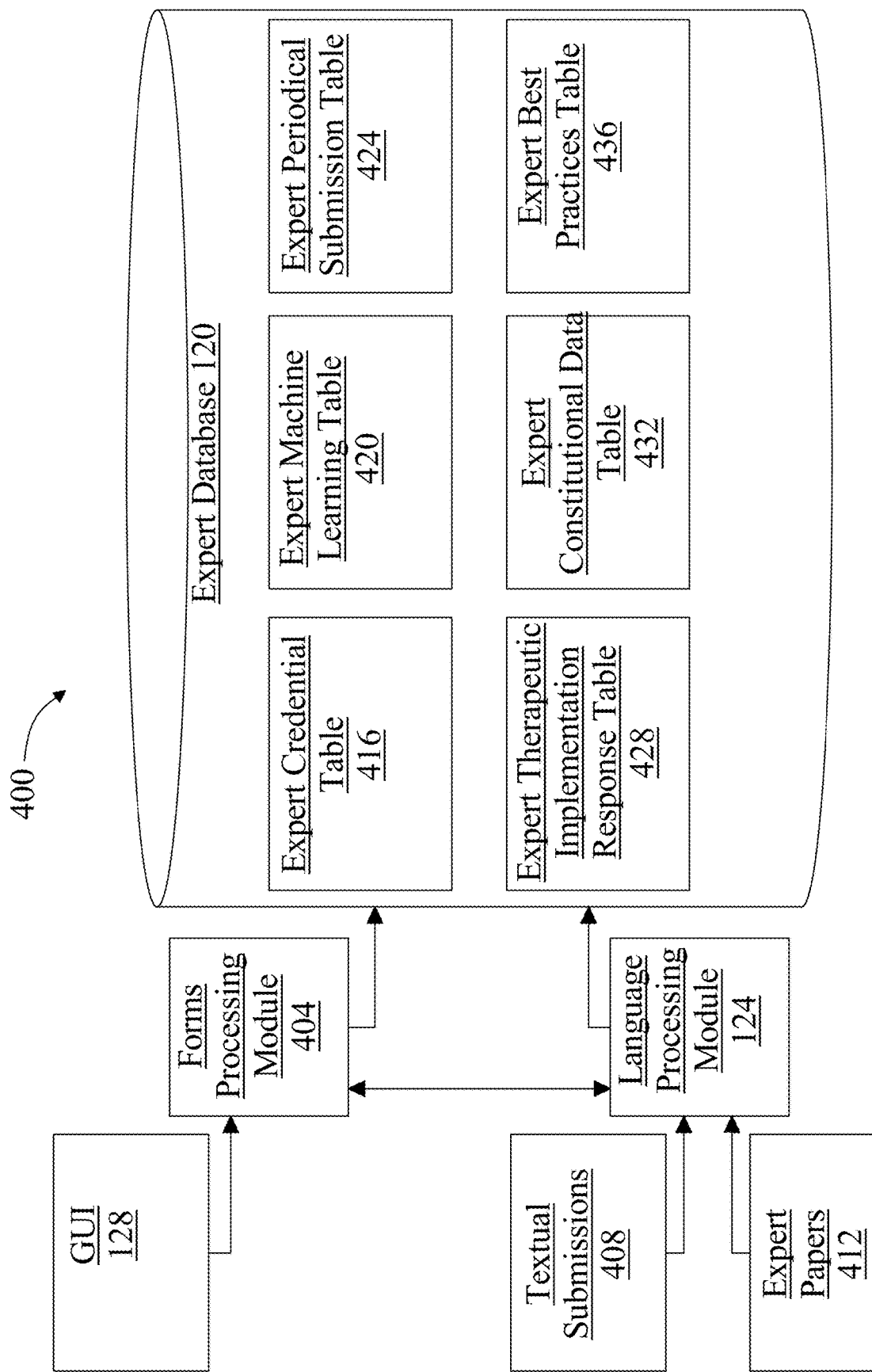
FIG. 4 is a block diagram illustrating an exemplary embodiment of an expert database.

Referring now to FIG. 4, an exemplary embodiment of expert database 120 is illustrated. Expert database 120 may be implemented as any data structure as described above in reference to FIG. 1. One or more database tables may be linked to one another by, for instance, common column values. For instance, a common column between two tables of expert database 120 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 4, expert database 120 includes a forms processing module 404 that may sort data entered in a submission via graphical user interface 128 by, for instance, sorting data from entries in the graphical user interface 128 to related categories of data; for instance, data entered in an entry relating in the graphical user interface 128 to a clustering algorithm may be sorted into variables and/or data structures for storage of clustering algorithms, while data entered in an entry relating to a category of training data and/or an element thereof may be sorted into variables and/or data structures for the storage of, respectively, categories of training data. Where data is chosen by an expert from pre-selected entries such as drop-down lists, data may be stored directly; where data is entered in textual form, language processing module 124 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 124 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 124. Data may be extracted from expert papers 412, which may include without limitation publications in medical and/or scientific journals, by language processing module 124 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 4, one or more tables contained within expert database 120 may include expert credential table 416; expert credential table 416 may include one or more data entries relating to expert credentials. One or more tables contained within expert database 120 may include expert machine learning table 420; expert machine learning table 420 may include one or more data entries relating to machine learning include training sets, machine-learning algorithms, supervised machine-learning processes, unsupervised machine-learning processes and the like. One or more tables contained within expert database 120 may include expert periodical submission table 424; expert periodical submission table 424 may include one or more data entries relating to expert periodical submissions. One or more tables contained within expert database 120 may include expert therapeutic implementation response 428; expert therapeutic implementation response 428 may include one or more data entries relating to expert therapeutic implementation responses. One or more tables contained within expert database 120 may include expert constitutional data table 432; expert constitutional data table 432 may include one or more data entries relating to constitutional data. One or more tables contained within expert database 120 may include expert best practices table 436; expert best practices table 436 may include one or more data entries relating to best practices.

Figure 5:
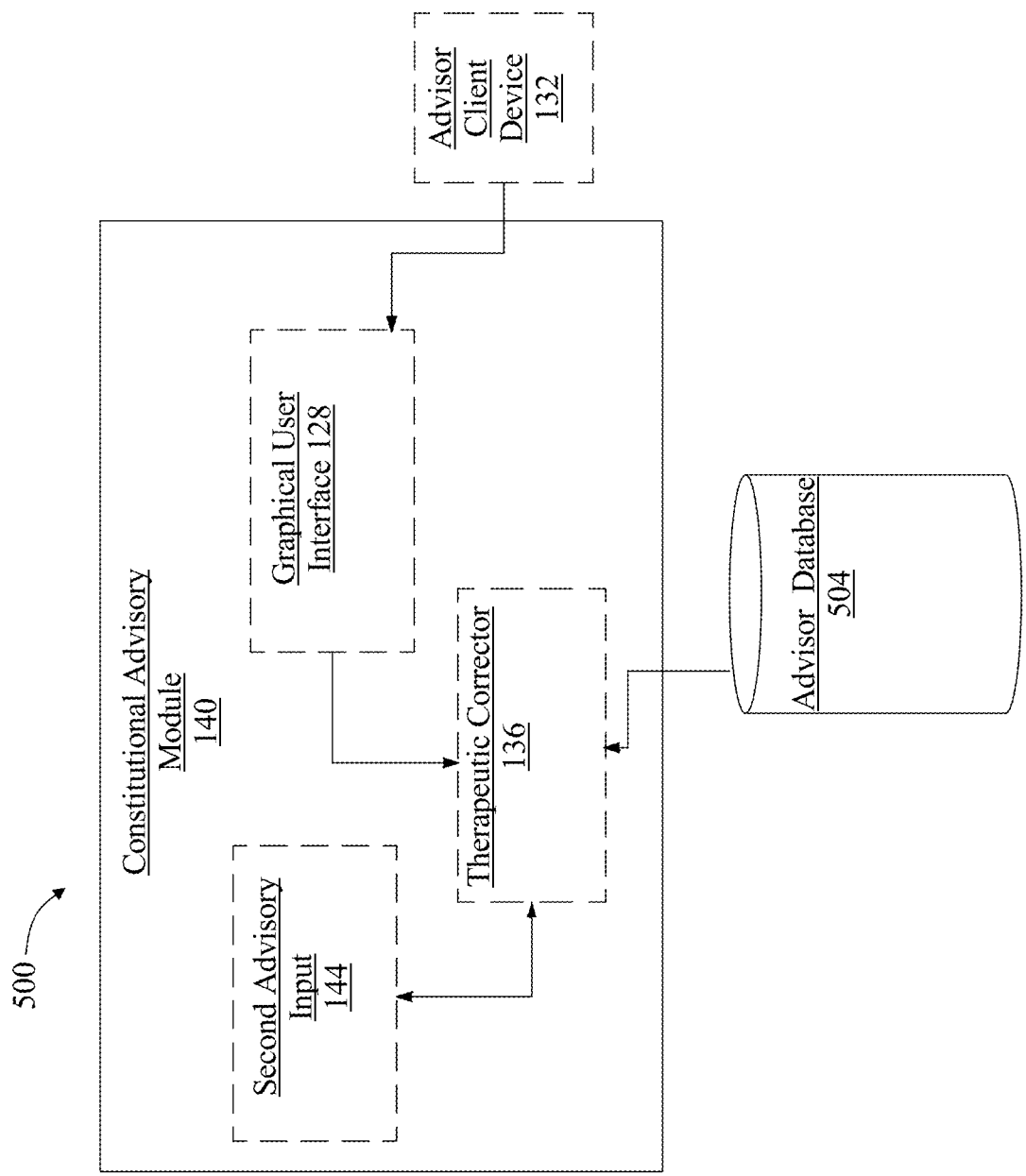
FIG. 5 is a block diagram illustrating an exemplary embodiment of a constitutional advisory module.

Referring now to FIG. 5, an exemplary embodiment 500 of constitutional advisory module 140 is illustrated. Constitutional advisory module 140 may be implemented as any hardware and/or software module. Constitutional advisory module 140 is configured to receive a therapeutic corrector 136 from constitutional generator module 108. Constitutional advisory module 140 may receive a therapeutic corrector 136 from constitutional generator module 108 utilizing any network methodology as described herein. Constitutional advisory module 140 displays the therapeutic corrector 136 on graphical user interface 128 located on processor 104. In an embodiment, constitutional advisory module 140 may display the therapeutic corrector 136 to a particular informed advisor who generated a first advisory input 112. Constitutional advisory module 140 receives a second advisory input 144 from an advisor client device operated by an informed advisor wherein the second advisory input contains a therapeutic corrector implementation response. Second advisory input 144 contains a therapeutic corrector implementation response. Therapeutic corrector implementation response may include any of the therapeutic corrector implementation responses as described above in reference to FIG. 1. For example, second advisory input 144 may include an informed advisor's description regarding implementing a particular treatment regimen for a user suggested within a therapeutic corrector 136. One or more advisory inputs may be stored in advisor database 504. Advisory database may include any data structure suitable for use as expert database 120 as described above.

Figure 6:
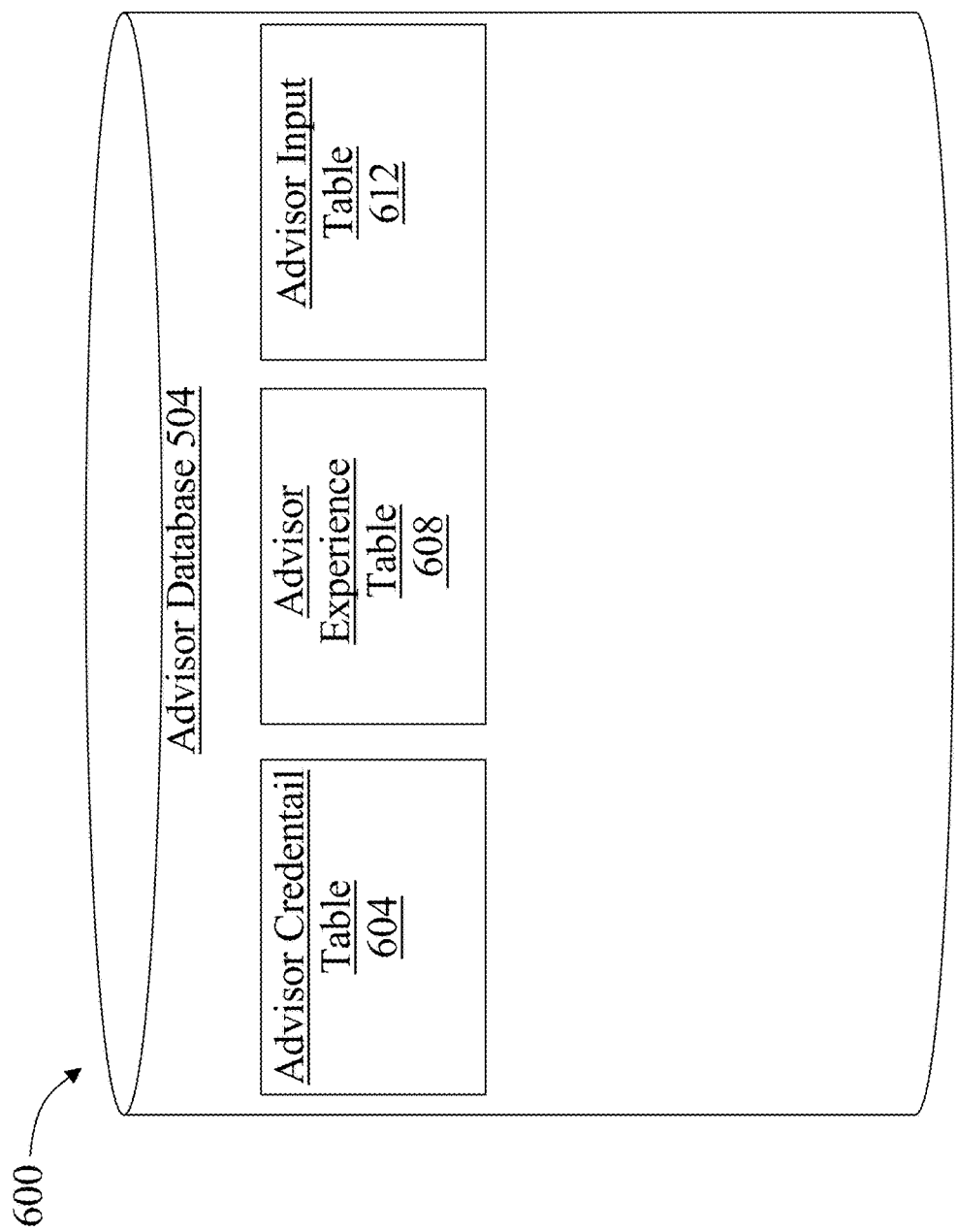
FIG. 6 is a block diagram illustrating an exemplary embodiment of an advisor database.

Referring now to FIG. 6, an exemplary embodiment 600 of advisor database 504 is illustrated. One or more tables contained within advisor database 504 may include advisor credential table 604; advisor credential table 604 may include one or more data entries describing an informed advisor's credentials. For instance and without limitation, credential table 604 may include information pertaining to an informed advisor's board certifications, education, clinical training, clinical experience, publications, licenses, and the like. One or more tables contained within advisor database 504 may include advisor experience table 608; advisor experience table 608 may include one or more data entries describing an informed advisor's clinical experience. For example, advisor experience table 608 may include information describing an informed advisor's clinical practice including number of patients treated each year, clinical success, medical conditions treated and the like. One or more tables contained within advisor database 504 may include advisor input table 612; advisor input table 612 may include one or more data entries describing inputs generated by an informed advisor. For example, advisor input table 612 may include stored data entries containing a first advisor input and a second advisor input.

Figure 7:
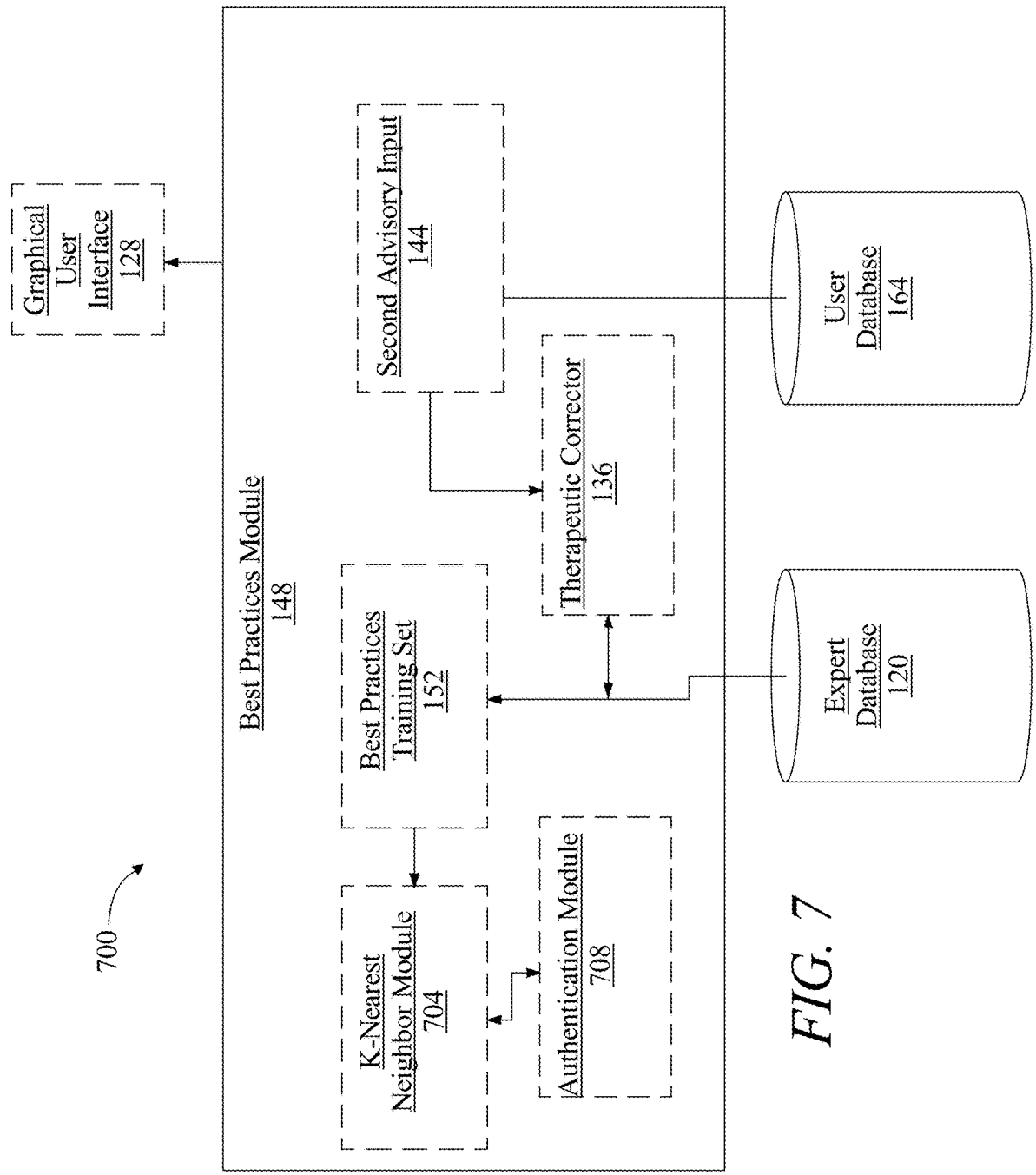
FIG. 7 is a block diagram illustrating an exemplary embodiment of a best practices module.

Referring now to FIG. 7, an exemplary embodiment 700 of best practices module 148 is illustrated. Best practices module 148 may be implemented as any hardware and/or software module. Best practices module 148 receives the second advisory input 144 containing the therapeutic corrector implementation response from the constitutional advisory module 140. This may be performed utilizing any network methodology as described herein. Best practices module 148 receives the therapeutic corrector 136 from the constitutional generator module 108. This may be performed utilizing any network methodology as described herein.

With continued reference to FIG. 7, best practices module 148 retrieves from expert database 120 a best practices training set 152. Best practices training set 152 correlates a therapeutic corrector 136 to therapeutic corrector implementation responses. Best practice training set may be generated based on input from one or more experts as described above. For example, best practices training set 152 may correlate a therapeutic corrector 136 such as initiating a fish oil supplement to one or more therapeutic corrector implementation responses that include decreased triglyceride levels, decreased total cholesterol levels, and increased high density lipoprotein (HDL) levels. In yet another non-limiting example, best practice training set may correlate a therapeutic corrector 136 such as initiation of a meditation sequence for a user with major depressive disorder with one or more therapeutic corrector implementation responses that include reduced number of depressive episodes, decreased nights experiencing insomnia, increased energy, and increased attendance at social gatherings.

With continued reference to FIG. 7, best practices module 148 may include k-nearest neighbor module 704. K-nearest neighbor module 704 may be implemented as any hardware and/or software module. K-nearest neighbor module may calculate an optimal vector output for the therapeutic corrector 136 received from the constitutional generator module 108 utilizing a k-nearest neighbor algorithm 156 and the best practices training set 152. K-nearest neighbor module may modify best practices training set 152 by representing best practices training set 152 as vectors. Vectors may include mathematical representations of best practices training set 152. Vectors may include n-tuple of values which may represent a measurement or other quantitative value associated with a given category of data, or attribute. Vectors may be represented in n-dimensional space using an axis per category of value represented in n-tuple of values, such that a vector has a geometric direction characterizing the relative quantities of attributes in the n-tuple as compared to each other. In an embodiment, K-nearest neighbor module may calculate an initial heuristic ranking association between therapeutic corrector 136 and elements of best practices training set 152. Initial heuristic may include selecting some number of highest-ranking associations and/or training set elements. K-nearest neighbor module may perform one or more processes to modify and/or format classified best practices training set 152. Classified best practices training set 152 may contain "N" unique features, whereby a dataset contained within classified best practices training set 152 and represented as a vector may contain a vector of length "N" whereby entry "I" of the vector represents that data point's value for feature "I." Each vector may be mathematically represented as a point in "R^N." For instance and without limitation, K-nearest neighbor module may modify entries contained within classified best practices training set 152 training data to contain consistent forms of a variance. After appropriate selection of best practices training set 152, K-nearest neighbor module performs K-nearest neighbors algorithm by classifying therapeutic datasets contained within the selected classified best practices training set 152. Selected classified best practices training set 152 training data may be represented as an "M×N" matrix where "M" is the number of data points contained within the classified best practices training set 152 training data and "N" is the number of features contained within the selected classified best practices training set 152 training data. Classifying datasets contained within selected classified best practices training set 152 training data set may include computing a distance value between an item to be classified such as a therapeutic dataset and each dataset contained within selected classified best practices training set 152 training set which may be represented as a vector. A value of "k" may be pre-determined or selected that will be used for classifications. In an embodiment, value of "k" may be selected as an odd number to avoid a tied outcome. In an embodiment, value of "k" may be decided by K-nearest neighbor module arbitrarily or value may be cross validated to find an optimal value of "k.". K-nearest neighbor module may then select a distance metric that will be used in K-nearest neighbors algorithm. In an embodiment, K-nearest neighbor module may utilize Euclidean distance which may be measure distance by subtracting the distance between a training data point and the datapoint to be classified such as a therapeutic corrector 136. In an embodiment, Euclidean distance may be calculated by a formula represented as: $E(x, y) = \sqrt{\Sigma_{i=0}^{n}(xi-yi)^2}$. In an embodiment, K-nearest neighbor module may utilize metric distance of cosine similarity which may calculate distance as the difference in direction between two vectors which may be represented as: similarity=cos $\theta = A \times B \div \|A\| \|B\|$. After selection of "k" value, and selection of distance measurement by K-nearest neighbor module, K-nearest neighbor module may partition in "R^N" into sections. Sections may be calculated using the distance metric and the available data points contained within selected classified best practices training set 152. K-nearest neighbor module may calculate a plurality of optimal vector outputs; in such an instance, where a plurality of matching entries is returned, optimal vector output may be obtained by aggregating matching entries including any suitable method for aggregation, including component-wise addition followed by normalization component-wise calculation of arithmetic means, or the like. K-nearest neighbor module generates an optimal vector output containing an expected therapeutic corrector implementation response 160.

With continued reference to FIG. 7, best practices module 148 may include authentication module 708. Authentication module 708 may be implemented as any hardware and/or software module. Authentication module 708 authenticates a second advisory input 144 containing a therapeutic corrector implementation response based on an expected therapeutic corrector implementation response 160 generated by k-nearest neighbor module 704. Authentication module 708 may authenticate a second advisory input 144 containing a therapeutic corrector implementation response by determining if a therapeutic corrector implementation response matches one or more expected therapeutic corrector implementation response 160 generated by k-nearest neighbor module 704. For example, authentication module 708 may receive second advisory input 144 from constitutional advisory module 140 that contains a therapeutic corrector implementation response that contains a description of a side effect an informed advisor noticed when a user started on a nutritional supplement that included the development of a dry cough. In such an instance, authentication module 708 may compare the side effect of a dry cough to one or more expected therapeutic corrector implementation response 160 generated by k-nearest neighbor module 705 includes a dry cough. If for example, dry cough was listed as one or more expected therapeutic corrector implementation response 160, then authentication module 708 may authenticate the second advisory input 144 containing the therapeutic corrector implementation response. In such an instance, authentication module 708 may then update the best practices module 148 to incorporate the therapeutic corrector implementation response as a data entry in expert database 120, as a training set entry in best practices training set 152, and/or incorporating the therapeutic corrector implementation response into a particular machine-learning model.

With continued reference to FIG. 7, authentication module 708 may authenticate a therapeutic corrector implementation response that does not match an expected therapeutic implementation response generated by k-nearest neighbor module 704 by obtaining a second authenticator, to determine if a particular therapeutic corrector implementation response may include an observation or response that may not be widely known or accepted by the medical community yet. For example, an informed advisor may have success utilizing a known medication for a new use in a user with a rare disease that may have never been observed by any other experts and may not be generated as an expected therapeutic implementation response. In such an instance, authentication module 708 may be unable to authenticate the therapeutic corrector implementation response and may have to seek to authenticate the therapeutic corrector implementation response by other measures including verifying expert periodicals to determine if there has been any other literature available that describes the new use for the known medication in a rare genetic disease, or obtaining a second opinion from a second informed advisor who may also be a known expect in a field relating to a therapeutic corrector implementation response, or examining user constitutional data to determine if a user reports feeling better since starting the new medication or if any health measurements of a user have improved.

With continued reference to FIG. 7, authentication module 708 may authenticate a therapeutic corrector implementation response by receiving a second expected therapeutic corrector implementation response 160 from a second informed advisor. Authentication module 708 may display the second advisory input 144 containing a therapeutic corrector implementation response and an expected therapeutic corrector implementation response 160 on a graphical user interface 128 located on processor 104 to a second informed advisor. Second informed advisor may include any informed advisor other than first informed advisor. Second informed advisor may be of a particular specialty and may practice in an area of medicine or healthcare similar to first informed advisor. Second informed advisor may also be considered a specialist in regard to the topic of a particular therapeutic corrector implementation response. Authentication module 708 may select a second informed advisor to receive a second expected therapeutic corrector implementation response 160 by locating a potential second informed advisor's credentials from advisor database 504 or looking for a potential second informed advisor who has a certain level of experience or knowledge which may be stored within advisor database. Second informed advisor may generate a second expected therapeutic corrector implementation response 160 which authentication module 708 may receive and utilize to authenticate the second advisory input 144. Authentication module 708 may authenticate a second informed advisor's credentials by receiving a second expert credential validator from second informed advisor. Second expert credential validator may include any expert credential validator as described above in reference to FIG. 1. Authentication module 708 may compare a second expert credential validator to a list of known expert credentials stored in expert database 120 and determine that the second expert credential validator is authentic.

With continued reference to FIG. 7, authentication module 708 may authenticate a therapeutic corrector implementation response by determining if a potential therapeutic corrector implementation response is contained within a particular periodical submission. Authentication module 708 may retrieve an expert periodical submission contained within expert database 120 and locate an expected therapeutic corrector implementation response 160 contained within the expert periodical submission. In an embodiment, expert periodical submissions contained within expert database 120 may be organized according to particular categories and/or topics so that locating particular entries relating to particular topics contained within therapeutic corrector implementation responses may be performed rapidly and with ease. In an embodiment, language processing module 124 may be utilized to locate one or more words or strings of words that may be extracted from a particular therapeutic corrector implementation response that may summarize the topic or field of medicine that the therapeutic corrector implementation response relates to. Such words and/or strings of words may be utilized to located expert periodical submission that are related to the topic or field of medicine contained within the words or strings of words. Authentication module 708 may compare a therapeutic corrector implementation response to a second expected therapeutic corrector implementation response 160 contained within an expert periodical submission. Authentication module 708 may then utilize a second expected therapeutic corrector implementation response 160 to authenticate a first therapeutic implementation response if a second expected therapeutic corrector implementation response 160 matches an expected therapeutic implementation response. A therapeutic corrector implementation response that is authenticated such as by matching to a second expected therapeutic corrector implementation response 160 may be utilized to update best practices module 148 such as by incorporating a therapeutic corrector implementation response into expert database 120 and/or incorporating the second expected therapeutic implementation response into a training set.

With continued reference to FIG. 7, authentication module 708 may authenticate a second advisory input 144 containing a therapeutic corrector implementation response by comparing the therapeutic corrector implementation response to user constitutional data. Authentication module 708 may retrieve an element of user constitutional data from user database 164. User constitutional data may include any of the user constitutional data as described above. For example, user constitutional data may include one or more physically extracted samples such as a hair sample analyzed for heavy metals or a urine sample analyzed for the presence or absence of ketones. User constitutional data may also include one or more descriptions of how a user may be feeling or responding to particular treatment. For example, user constitutional data may include medical records containing subjective and objective assessments of a user, such as from consultations and appointments with functional medicine doctors who may report how a user is feeling based on in-person or phone calls discussing a user's progress with a particular diagnosis or treatment. User constitutional data may include user reports such as self-assessments or journal entries describing how a user feels or is feeling in regard to particular medical intervention, diagnosis, treatment, and the like. Authentication module 708 may retrieve an element of user constitutional data from a user database 164 and compare an element of user constitutional data to a therapeutic corrector implementation response. For example, a therapeutic corrector implementation response that contains a description of a user who experienced unknown side effects from an acupuncture treatment such as ringing in the ears may be utilized to locate an element of user constitutional data contained within user database 164 to determine if user ever complained of ringing in the ears during an acupuncture treatment. In yet another non-limiting example, a therapeutic corrector implementation response that contains a description of a user who experienced remission of user's diabetes after being treatment for a medication intended to treat user's hepatitis, may be utilized to extract an element of user constitutional data that includes user's most recent fasting blood glucose and hemoglobin A1C results to determine if user's blood sugars accurately show that user's diabetes is in fact in remission. A therapeutic corrector implementation response that is authenticated by an element of user constitutional data may be utilized to update expert knowledge module utilizing any of the methods as described above.

Figure 8:
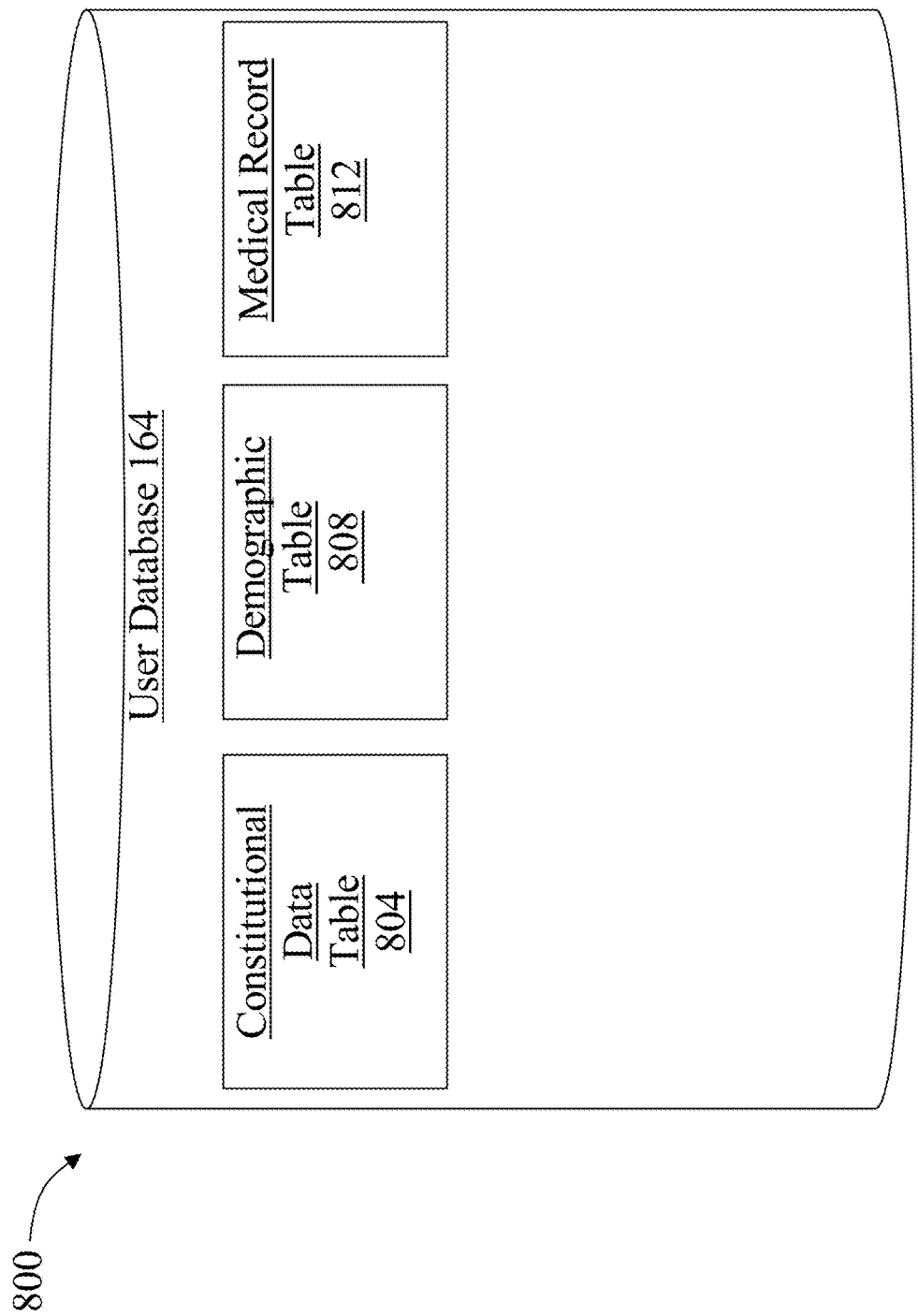
FIG. 8 is a block diagram illustrating an exemplary embodiment of a user database.

Referring now to FIG. 8, an exemplary embodiment 800 of user database 164 is illustrated. User database 164 may be implemented as any data structure suitable for use as expert database 120 as described above in reference to FIG. 1. One or more tables contained within user database 164 may include constitutional data table 804; constitutional data table 804 may include one or more data entries containing an element of user constitutional data. For example, constitutional data table 804 may include one or more results from a medical imaging test, one or more analyzed blood samples analyzed for intracellular and extracellular nutrient levels, one or more saliva samples analyzed for hormone levels and the like. One or more tables contained within user database 164 may include demographic table 808; demographic table 808 may include one or more data entries containing user demographic information. For example, demographic table 808 may include information describing user's full legal name, address, occupation, education level, marital status, and the like. One or more tables contained within user database 164 may include medical record table 812; medical record table 812 may include one or more data entries describing a user's medical records. For example, medical record table 812 may include one or more clinical notes from an appointment with an informed advisor, one or more subjective findings from a physical exam, one or more notes summarizing how a user feels and the like.

Figure 9:
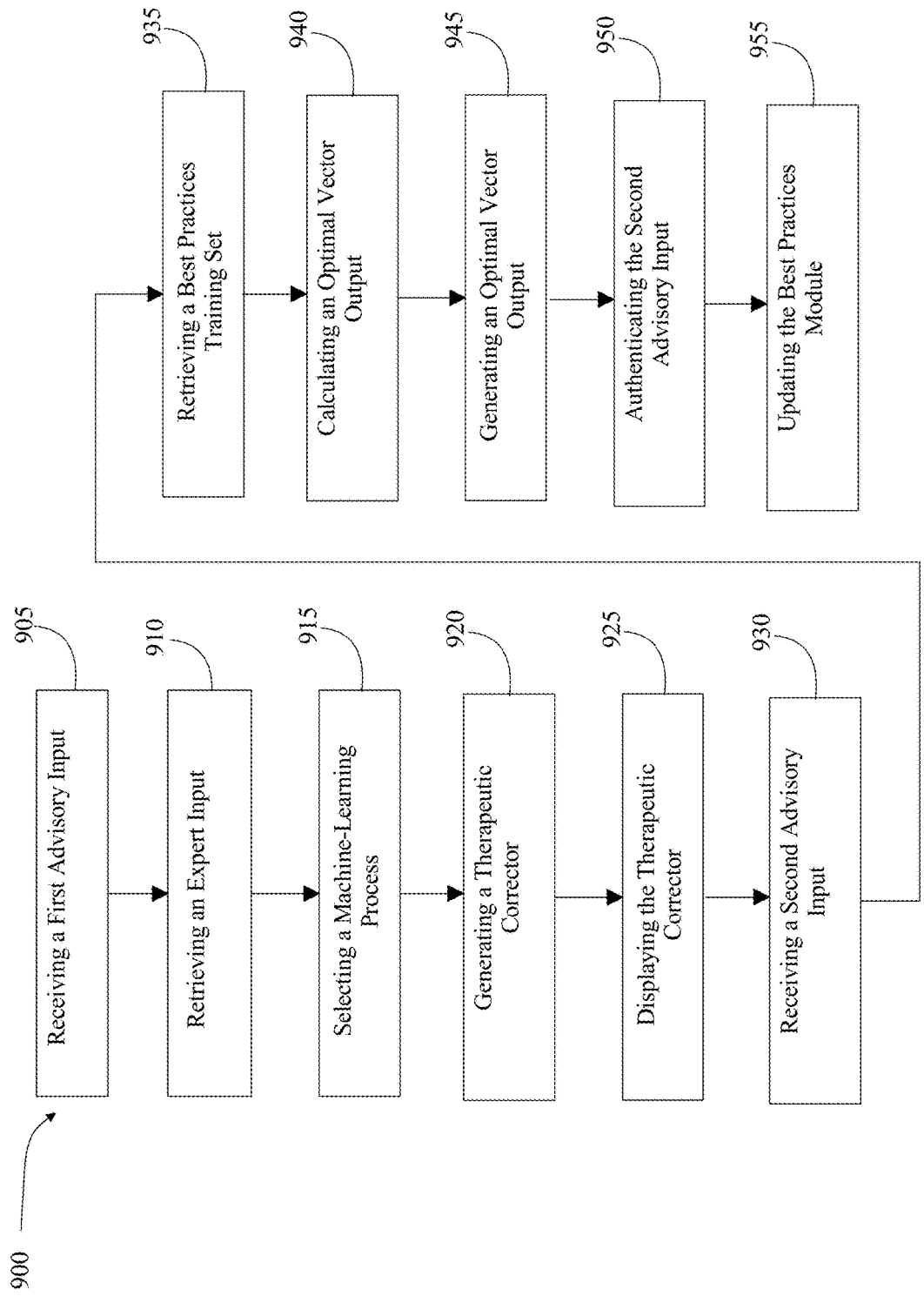
FIG. 9 is a process flow diagram illustrating an exemplary embodiment of a method of confirming an advisory interaction with an artificial intelligence platform.

Referring now to FIG. 9, an exemplary embodiment 900 of a method of confirming an advisory interaction with an artificial intelligence platform is illustrated. At step 905 a processor 104 receives a first advisory input 112 containing a constitutional inquiry and a user identifier. Processor 104 may receive a first advisory input 112 utilizing any network methodology as described herein. Processor 104 may receive a first advisory input containing a constitutional inquiry and a user identifier from an advisor client device operated by an informed advisor. A first advisory input 112 contains a constitutional inquiry. Constitutional inquiry may include any of the constitutional inquires as described above in reference to FIGS. 1-8. A constitutional inquiry may include any inquiry pertaining to the human body generated by an informed advisor. An informed advisor may include any of the informed advisors as described above in reference to FIGS. 1-8. For example, a constitutional inquiry may include an inquiry as to possible diagnoses for a user who may be suffering from symptoms that include back ache, fatigue, and muscle spasms. In yet another non-limiting example, a constitutional inquiry may include an inquiry as to possible treatments an informed advisor should consider when treating a particular illness the informed advisor may be unfamiliar with treating or may have not treated in a long time and may be somewhat perplexed as to where the informed advisor should initiate treatment. First advisory input 112 contains a user identifier. User identifier may include any of the user identifiers as described above in reference to FIGS. 1-8.

With continued reference to FIG. 9, a processor 104 may validate an informed advisor's credentials upon receiving a first advisory input 112. In conjunction with receiving a first advisory input 112, a processor 104 may receive a first expert credential validator. First expert credential validator may include any of the first expert credential validators as described above in reference to FIGS. 1-8. Processor 104 may compare a first expert credential validator to a list of known expert credentials stored in an expert database 120. Processor 104 may determine that the first expert credential validator is authentic upon locating the first expert credential validator on the expert list.

With continued reference to FIG. 9, at step 910 a processor 104 retrieves an expert input 116 from best practices module 148 operating on the processor 104 as a function of a first advisory input 112 and a user identifier. Expert input 116, includes any expert submission as described above in more detail in reference to FIG. 1. Expert input 116 may be generated by one or more informed advisors who may be considered experts in a particular field of medicine and/or health care such as by demonstrating certain professional milestones, having particular credentials and/or licenses, passing specific certifying exams, publishing articles, papers, and/or journal submissions on particular topics and the like. Expert input 116 may include expert advice as to particular training sets that can be selected based on particular first advisory input 112 or particular machine-learning models that may be best suited to be calculated for particular first advisory input 112. For instance and without limitation, expert input 116 may dictate that a first advisory input 112 containing a request for a list of particular diagnoses based on specific symptoms may be best suited to a supervised machine-learning algorithm while a first advisory input 112 containing a request for a list of possible treatments for a specific medical condition may be best suited for a lazy-learning algorithm such as k-nearest neighbor. Expert input 116 may be stored within expert database 120, which may include any data structure as described in more detail above. Expert input 116 may be constantly updated in real time to account for new discoveries and new research that may be published. Further, expert input 116 may be revoked such as when an expert's credentials may lapse, or an expert may suddenly die, or subsequent research comes out that invalidates previously demonstrate research. In an embodiment, expert input 116 may be retrieved based on previous interactions with a user and system 100. Processor 104 may utilize a user identifier to retrieve information from user database 164 that may contain information about previous expert input 116 utilized in reference to a particular user.

With continued reference to FIG. 9, at step 915 a processor 104 selects a machine-learning process as a function of an expert input 116. A machine-learning process may include any of the machine-learning processes as described above in reference to FIGS. 1-8. Machine-learning processes may include supervised machine-learning processes, unsupervised machine-learning processes, lazy-learning processes and the like. One or more machine-learning processes, machine-learning models, and/or training sets may be stored within expert database 120. Processor 104 may select a particular machine-learning process based on expert input 116. For example, expert input 116 may describe a particular machine-learning model that may be best suited to generate specific therapeutic corrector 136 identified within a first advisory input 112. One or more machine-learning models may be previously calculated and stored within expert database 120 to allow for rapid selection and generation of a therapeutic corrector 136.

With continued reference to FIG. 9, at step 920 a processor 104 generates a therapeutic corrector 136 utilizing a machine-learning process and the first advisory input 112 wherein the therapeutic corrector 136 includes a response to a constitutional inquiry. Therapeutic corrector 136 may include any of the therapeutic corrector 136 as described above in reference to FIGS. 1-8. For example, a first advisory input 112 may include an inquiry as to possible diagnoses based on a user's symptoms. A processor 104 may generate a therapeutic corrector 136 that contains a response to the first advisory input 112 that include a list of possible diagnoses. In yet another non-limiting example, a first advisory input 112 that contains an inquiry regarding possible treatment options for a rare disease may be utilized to generate a therapeutic corrector 136 that includes a list of possible treatment options for the rare disease.

With continued reference to FIG. 9, a processor 104 may generate a therapeutic corrector 136 utilizing supervised and/or unsupervised machine-learning processes. For example, a processor 104 may generate a therapeutic corrector 136 utilizing a supervised machine-learning algorithm. A processor 104 may receive therapeutic training data from expert database 120 that includes a plurality of data entries containing constitutional inquires correlated to therapeutic corrector 136. Therapeutic training data may include any of the training data as described above. A processor 104 may generate using a supervised machine-learning algorithm a therapeutic model that outputs a therapeutic corrector 136 utilizing the therapeutic training data and the first advisory input 112 containing a constitutional inquiry. Therapeutic model may include any machine learning process and may include linear or polynomial regression algorithms. Therapeutic model may include one or more equations. Therapeutic model may include a set of instructions utilized to generate outputs based on inputs derived using a machine-learning algorithm and the like. In yet another non-limiting example, a processor 104 may generate a therapeutic corrector 136 utilizing one or more unsupervised machine-learning processes. Processor 104 may receive a plurality of unclassified data entries from expert database 120. Unclassified data entries may include any of the unclassified data entries as described above in reference to FIGS. 1-8. Processor 104 generates using an unsupervised machine-learning algorithm an unsupervised model that outputs a therapeutic corrector 136 utilizing the plurality of unclassified data entries and a first advisory input 112 containing a constitutional inquiry. Unsupervised model may include any machine learning process and may include linear or polynomial regression algorithms. Unsupervised model may include one or more equations. Unsupervised model may include a set of instructions utilized to generate outputs based on inputs derived using a machine-learning algorithm and the like. A processor 104 may generate a therapeutic corrector 136 utilizing lazy learning processes including any of the lazy-learning processes as described above in reference to FIGS. 1-8.

With continued reference to FIG. 9, at step 925 a processor 104 displays a therapeutic corrector 136 on a graphical user interface 128 located on a processor 104. Processor 104 may display a therapeutic corrector 136 on a graphical user interface 128 utilizing any methodology as described herein.

With continued reference to FIG. 9, at step 930 a processor 104 receives a second advisory input 144 from an advisor client device operated by an informed advisor wherein the second advisory input 144 contains a therapeutic corrector implementation response. A processor 104 receives a second advisory input 144 utilizing any network methodology as described herein. Second advisory input 144 includes any of the second advisory input 144 as described above in reference to FIGS. 1-8. Second advisory input 144 includes a therapeutic corrector implementation response. Therapeutic corrector implementation response includes any of the therapeutic corrector implementation responses as described above in reference to FIGS. 1-8. Therapeutic corrector implementation response may include an informed advisor's experience with implementing or not implementing a particular therapeutic corrector 136. For example, a therapeutic corrector implementation response may include a description of a particular reaction a user had when taking a particular medication recommended in a therapeutic corrector 136. In yet another non-limiting example, a therapeutic corrector implementation response may include a description as to whether suggested lab tests contained within a therapeutic corrector 136 helped an informed advisor diagnose or not diagnose a particular medical condition.

With continued reference to FIG. 9, at step 935 a processor 104 receives from an expert database 120 located on a processor 104 a best practices training set 152 wherein the best practices training set 152 correlates a therapeutic corrector 136 to therapeutic corrector implementation responses. Best practices training set 152 may include any of the training data as described above in reference to FIG. 1.

With continued reference to FIG. 9, at step 940 a processor 104 calculates an optimal vector output for a therapeutic corrector 136 received from a constitutional generator module 108 utilizing a k-nearest neighbor algorithm 156 and a best practices training set 152. Optimal vector output includes any of the optimal vector outputs as described above in reference to FIGS. 1-8. Optimal vector output may be generated utilizing a k-nearest neighbor algorithm 156 which may include any of the k-nearest neighbor algorithm 156 as described above in reference to 8.

With continued reference to FIG. 9, at step 945 a processor 104 generates an optimal vector output containing an expected therapeutic corrector implementation response 160. Expected therapeutic corrector implementation response 160 includes any probable or predictable response to implementing a particular therapeutic corrector 136. Probable or predictable response may be known based on currently available medical literature, case studies, journal articles, expert input 116, data aggregations from surveyed responses, and the like. For instance and without limitation, an expected therapeutic corrector implementation response 160 may include a list of expected side effects a user may experience upon taking a particular supplement or medication. In yet another non-limiting example, an expected therapeutic corrector implementation response 160 may include a list of lab values that may be affective either positively or negatively upon initiating a particular exercise regimen. In yet another non-limiting example, an expected therapeutic corrector implementation response 160 may include a list of conditions that a particular supplement has studied indications to be utilized for.

With continued reference to FIG. 9, at step 950 a processor 104 authenticates a second advisory input 144 containing a therapeutic corrector implementation response as a function of an expected therapeutic corrector implementation response 160. Authenticating may include evaluating by a processor 104 to determine if a therapeutic corrector implementation response matches an expected therapeutic corrector implementation response 160. For example, a processor 104 may authenticate a therapeutic corrector implementation response that contains an adverse reaction that a user experienced upon consuming a particular homeopathic medication to an expected therapeutic corrector implementation response 160 that lists the adverse reaction experienced by the user. Therapeutic corrector implementation responses that may match to one or more expected therapeutic corrector implementation response 160 may be authenticated utilizing other methods. This may include obtaining a second informed advisor response. A processor 104 may display a second advisory input 144 containing a therapeutic corrector implementation response and an expected therapeutic corrector implementation response 160 on a graphical user interface 128 located on the processor 104 to a second informed advisor. Second informed advisor may include any of the second informed advisors as described above in reference to FIGS. 1-8. A processor 104 may receive a second expected therapeutic corrector implementation response 160 from a second informed advisor and authenticate a second advisory input 144 containing a therapeutic corrector implementation response as a function of a second expected therapeutic corrector implementation response 160. This may be performed utilizing any of the methods as described above in more detail in reference to FIG. 7. A processor 104 may authenticate a second informed advisor by authenticating a second informed advisor's credentials. A processor 104 may receive a second expert credential validator, compare the second expert credential validator to a list of known expert credentials stored in expert database 120 and determine that the second expert credential validator is authentic. A processor 104 may authenticate a second advisory input 144 containing a therapeutic corrector implementation response utilizing expert periodical submissions. A processor 104 may retrieve an expert periodical submission contained within expert database 120. A processor 104 may locate an expected therapeutic corrector implementation response 160 contained within an expert periodical submission. This may be performed utilizing any of the methodologies as described above in reference to FIGS. 1-8. A processor 104 may compare a therapeutic corrector implementation response to a second expected therapeutic corrector implementation response 160 contained within an expert periodical submission. A processor 104 may confirm the legitimacy of a first therapeutic implementation response upon confirming that a therapeutic corrector implementation response is contained within an expert periodical submission. This may be performed utilizing any of the methodologies as described above in reference to FIGS. 1-8. A processor 104 may authenticate an advisory input by utilizing user constitutional data. A processor 104 may retrieve an element of user constitutional data from a user database 164. User constitutional data may include any of the user constitutional data as described above in reference to FIGS. 1-7. A processor 104 compares an element of user constitutional data to a therapeutic corrector implementation response and authenticates a first therapeutic implementation response as a function of the element of user constitutional data. This may be performed utilizing any of the methods as described above in reference to FIGS. 1-8.

With continued reference to FIG. 9, at step 955 a processor 104 updates a best practices module 148 as a function of authenticating a first advisory input 112 containing a therapeutic corrector implementation response. Updating the best practices module 148 may include incorporating a therapeutic corrector implementation response into the best practices module 148. A therapeutic corrector implementation response may be incorporated into best practices module 148 by incorporating a therapeutic corrector 136 and/or a therapeutic corrector implementation response into one or more best practices training set 152. A therapeutic corrector implementation response may be incorporated into the best practices module 148 by incorporating a therapeutic corrector 136 and a therapeutic corrector implementation response into a machine-learning model stored within expert database 120. This may be performed utilizing any of the methodologies as described above in reference to FIGS. 1-8.

Figure 10:
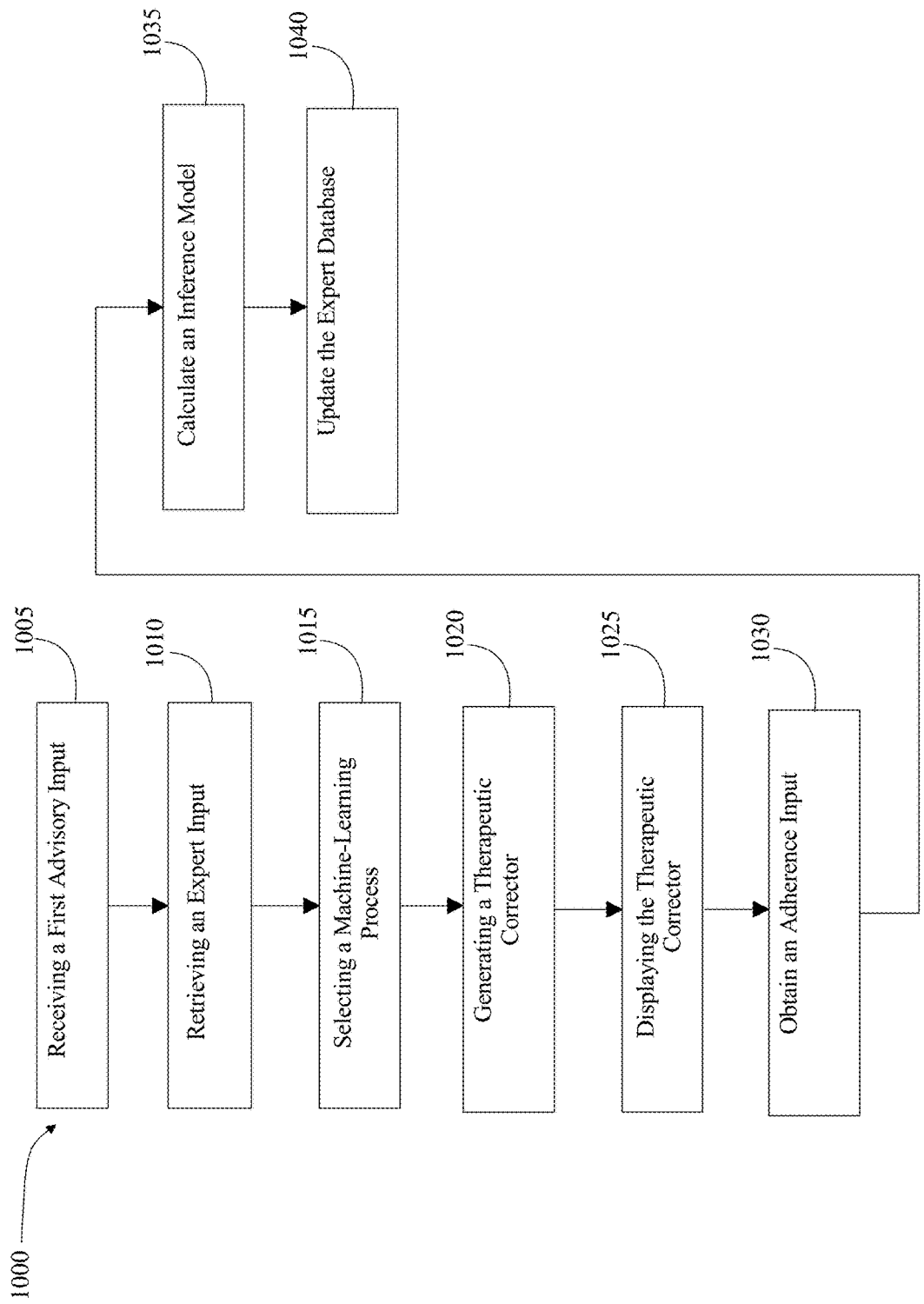
FIG. 10 is a process flow diagram illustrating an exemplary embodiment of a method of calculating an inference model.

Now referring to FIG. 10, an exemplary embodiment 1000 of a method of calculating an inference model is illustrated. At step 1005 a processor 104 receives a first advisory input 112 containing a constitutional inquiry and a user identifier from an advisor client device operated by an informed advisor. Processor 104 includes any of the processor 104 as described above, in reference to FIGS. 1-9. First advisory input 112 includes any of the first advisory input as described above, in reference to FIGS. 1-9. A first advisory input 112 contains a constitutional inquiry. Constitutional inquiry may include any of the constitutional inquires as described above in reference to FIGS. 1-9. An informed advisor includes any of the informed advisor as described above, in reference to FIGS. 1-9. User identifier includes any of the user identifier as described above, in reference to FIGS. 1-9.

With continued reference to FIG. 10, at step 1010, processor 104 retrieves an expert input 116 from an expert database 120 operating on processor 104 as a function of first advisory input 112 and a user identifier. Expert input 116, includes any expert input 116 as described above in reference to FIGS. 1-9. Expert database 120 includes any of the expert database 120 as described above, in reference to FIGS. 1-9.

With continued reference to FIG. 10, at step 1015, processor 104 selects a machine-learning process as a function of an expert input 116. A machine-learning process includes any of the machine-learning process as described above, in reference to FIGS. 1-9. Machine-learning processes may include supervised machine-learning processes, unsupervised machine-learning processes, lazy-learning processes and the like.

With continued reference to FIG. 10, at step 1020, processor 104 generates a therapeutic corrector 136 utilizing machine-learning process and the first advisory input 112 wherein therapeutic corrector 136 includes a response to a constitutional inquiry. Therapeutic corrector 136 includes any of the therapeutic corrector 136 as described above, in reference to FIGS. 1-9. Constitutional inquiry includes any of the constitutional inquiry as described above, in reference to FIGS. 1-9.

With continued reference to FIG. 10, at step 1025, processor 104 displays a therapeutic corrector 136 on a graphical user interface 128 located on a processor 104. Graphical user interface 128 includes any of the graphical user interface 128 as describe above, in reference to FIGS. 1-9.

With continued reference to FIG. 10, at step 1030, processor 104 obtains an adherence input 204 from an advisor client device 132 operating by the informed advisor. Adherence input 204 includes any of the adherence input 204 as described above, in reference to FIGS. 1-9. Advisor client device 132 includes any of the advisor client device 132 as described above, in reference to FIGS. 1-9.

Still referring to FIG. 10, at step 1035, processor 104 calculates an inference model 208 as a function of adherence input 204. Inference model 208 includes any of the inference model 208 as described above, in reference to FIGS. 1-9.

Still referring to FIG. 10, at step 1040, processor 104 updates expert database 120 as a function of inference model 208 and therapeutic corrector 136.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
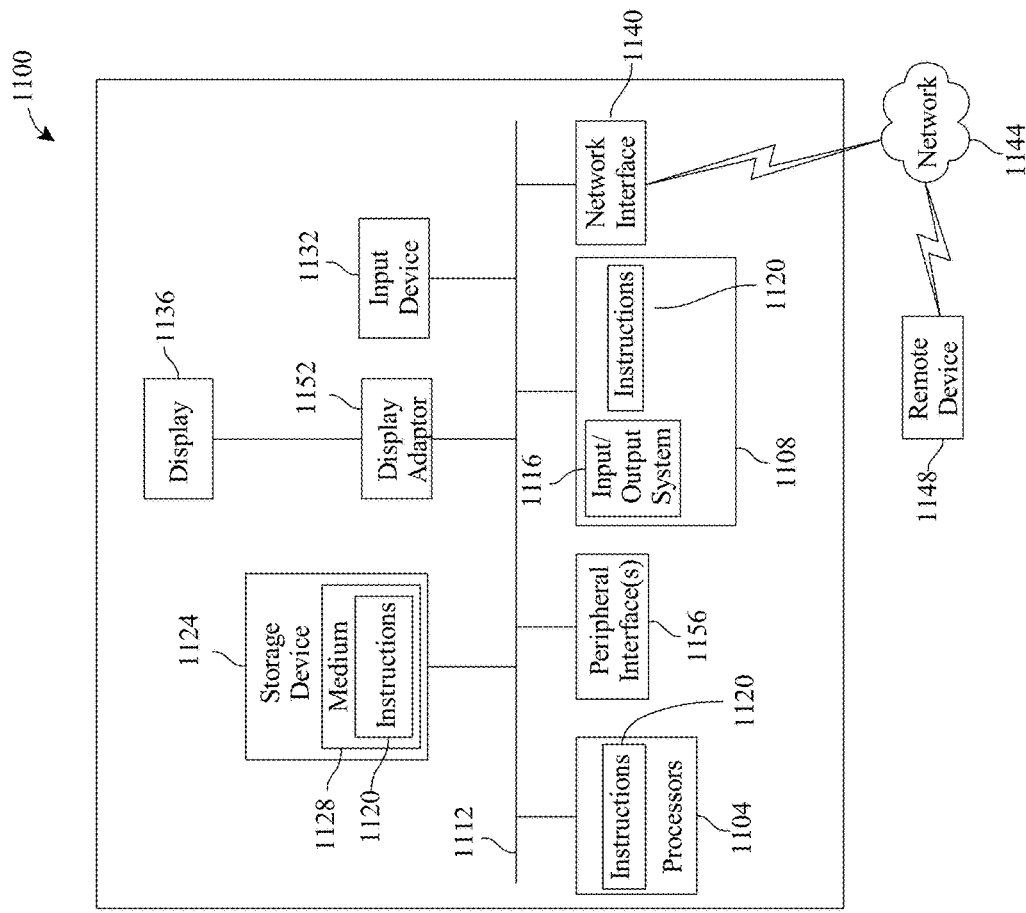
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 908 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 900 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for confirming an advisory interaction with an artificial intelligence platform the system comprising:
   a processor connected to a memory, wherein the processor is further configured to:
   receive a first advisory input containing a constitutional inquiry and a user identifier from an advisor client device operated by an informed advisor;
   retrieve an expert input from an expert database operating on the processor and located within a best practice module as a function of the first advisory input and the user identifier;
   select a machine-learning process as a function of the expert input;
   generate a therapeutic corrector utilizing the machine-learning process and the first advisory input wherein the therapeutic corrector further comprises a response to the constitutional inquiry, wherein the therapeutic corrector comprises a recommendation for lab tests a user should analyze as a function of symptom complaints;
   analyze lab work of a user to determine a diagnosis for an illness;
   display the therapeutic corrector on a graphical user interface located on the processor;
   receive a second advisory input from the advisor client device, wherein the second advisory input contains a therapeutic corrector implementation response, and wherein the therapeutic implementation response contains a description of at least one result as a function of implementing the therapeutic corrector;
   retrieve from the expert database located in the best practices module a best practices training set wherein the best practices training set correlates therapeutic correctors to therapeutic corrector implementation responses;
   update the best practices module to incorporate the therapeutic corrector implementation response as a training set entry in the best practices training set;
   obtain an adherence input from the advisor client device;
   calculate an inference model as a function of the adherence input; and
   update the expert database as a function of the inference model and therapeutic corrector.

2. The system of claim 1, wherein generating a therapeutic corrector further comprises:
   receiving therapeutic training data from an expert database wherein the therapeutic training data includes a plurality of data entries containing constitutional inquiries correlated to therapeutic correctors; and
   generating, using a supervised machine-learning algorithm, a therapeutic model that outputs a therapeutic corrector utilizing the therapeutic training data and the first advisory input containing the constitutional inquiry.

3. The system of claim 1, wherein generating a therapeutic corrector further comprises:
   receiving a plurality of unclassified data entries from an expert database; and
   generating using an unsupervised machine-learning algorithm the therapeutic corrector utilizing the plurality of unclassified data entries and the advisory input containing the constitutional inquiry.

4. The system of claim 1, wherein obtaining the adherence input further comprises:
   determining a therapeutic effect as a function of the therapeutic corrector; and
   obtaining the adherence input as a function of the therapeutic effect.

5. The system of claim 4, wherein determining the therapeutic effect further comprises:
   establishing a therapeutic enumeration;
   distinguishing a therapeutic divergence; and
   determining the therapeutic effect as a function of the therapeutic enumeration, the therapeutic divergence, and a therapeutic threshold.

6. The system of claim 1, wherein calculating the inference model further comprises:
   retrieving an adherence training set, wherein the adherence training set correlates a monitoring element to a therapeutic adjustment; and
   calculating the inference model as a function of the adherence input and the adherence training set using an adherence machine-learning model, wherein the adherence machine-learning model is trained as a function of the adherence training set.

7. The system of claim 1, wherein calculating the inference model further comprises:
   generating a physiological progression parameter; and
   calculating the inference model as a function of the physiological progression parameter.

8. The system of claim 7, wherein generating the physiological progression parameter further comprises:
   identifying a status of the therapeutic corrector;
   determining functional checkpoints as a function of the therapeutic corrector; and
   generating the physiological progression parameter as a function of the functional checkpoints.

9. The system of claim 1, wherein updating the expert database further comprises:
   generating a therapeutic framework; and
   updating the expert database as a function of the therapeutic framework.

10. The system of claim 9, wherein generating the therapeutic framework further comprises:
    producing a cryptographic identifier as a function of the user identifier; and
    generating the therapeutic framework as a function of the cryptographic identifier.

11. A method for confirming an advisory interaction with an artificial intelligence platform comprising:
    receiving, by a processor, a first advisory input containing a constitutional inquiry and a user identifier from an advisor client device operated by an informed advisor;
    retrieving, by the processor, an expert input from an expert database operating on the processor and located within a best practices module as a function of the first advisory input and the user identifier;
    selecting, by the processor, a machine-learning process as a function of the expert input;
    generating, by the processor, a therapeutic corrector utilizing the machine-learning process and the first advisory input wherein the therapeutic corrector further comprises a response to the constitutional inquiry, wherein the therapeutic corrector comprises a recommendation for lab tests a user should analyze as a function of symptom complaints;

analyzing lab work of a user to determine a diagnoses for an illness;

displaying, by the processor, the therapeutic corrector on a graphical user interface located on the processor;

receiving, by the processor, a second advisory input from the advisor client device, wherein the second advisory input contains a therapeutic corrector implementation response, and wherein the therapeutic implementation response contains a description of at least one result as a function of implementing the therapeutic corrector;

retrieve from the expert database located in the best practices module a best practices training set wherein the best practices training set correlates therapeutic correctors to therapeutic corrector implementation responses;

update the best practices module to incorporate the therapeutic corrector implementation response as a training set entry in the best practices training set;

obtaining, by the processor, an adherence input from the advisor client device;

calculating, by the processor, an inference model as a function of the adherence input; and updating, by the processor, the expert database as a function of the inference model and therapeutic corrector.

12. The method of claim 11, wherein generating a therapeutic corrector further comprises:

receiving therapeutic training data from an expert database wherein the therapeutic training data includes a plurality of data entries containing constitutional inquiries correlated to therapeutic correctors; and generating using a supervised machine-learning algorithm a therapeutic model that outputs a therapeutic corrector utilizing the therapeutic training data and the first advisory input containing the constitutional inquiry.

13. The method of claim 11, wherein generating a therapeutic corrector further comprises:

receiving a plurality of unclassified data entries from an expert database; and generating using an unsupervised machine-learning the therapeutic corrector utilizing the plurality of unclassified data entries and the advisory input containing the constitutional inquiry.

14. The method of claim 11, wherein obtaining the adherence input further comprises:

determining a therapeutic effect as a function of the therapeutic corrector; and obtaining the adherence input as a function of the therapeutic effect.

15. The method of claim 14, wherein determining the therapeutic effect further comprises:

establishing a therapeutic enumeration;

distinguishing a therapeutic divergence; and determining the therapeutic effect as a function of the therapeutic enumeration, the therapeutic divergence, and a therapeutic threshold.

16. The method of claim 11, wherein calculating the inference model further comprises:

retrieving an adherence training set wherein the adherence training set correlates a monitoring element to a therapeutic adjustment; and calculating the inference model as a function of the adherence input and the adherence training set using an adherence machine-learning model; wherein the adherence machine-learning model is trained as a function of the adherence training set.

17. The method of claim 11, wherein calculating the inference model further comprises:

generating a physiological progression parameter; and calculating the inference model as a function of the physiological progression parameter.

18. The method of claim 17, wherein generating the physiological progression parameter further comprises:

identifying a status of the therapeutic corrector;

determining functional checkpoints as a function of the therapeutic corrector; and generating the physiological progression parameter as a function of the functional checkpoints.

19. The method of claim 11, wherein updating the expert database further comprises:

generating a therapeutic framework; and updating the expert database as a function of the therapeutic framework.

20. The method of claim 19, wherein generating the therapeutic framework further comprises:

producing a cryptographic identifier as a function of the user identifier; and generating the therapeutic framework as a function of the cryptographic identifier.

* * * * *